US010155030B2

(12) United States Patent
Cao et al.

(10) Patent No.: US 10,155,030 B2
(45) Date of Patent: Dec. 18, 2018

(54) METHODS, ANTIBODIES, AND VACCINES UTILIZING EPITOPES OF ALPHA SYNUCLEIN FOR TREATMENT OF PARKINSONS DISEASE

(71) Applicants: Chuanhai Cao, Temple Terrace, FL (US); Xiaoyang Lin, Tampa, FL (US)

(72) Inventors: Chuanhai Cao, Temple Terrace, FL (US); Xiaoyang Lin, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 15/313,810

(22) PCT Filed: May 26, 2015

(86) PCT No.: PCT/US2015/032453
§ 371 (c)(1),
(2) Date: Nov. 23, 2016

(87) PCT Pub. No.: WO2015/179867
PCT Pub. Date: Nov. 26, 2015

(65) Prior Publication Data
US 2017/0196948 A1 Jul. 13, 2017

Related U.S. Application Data

(60) Provisional application No. 62/002,535, filed on May 23, 2014.

(51) Int. Cl.
*A61K 35/15* (2015.01)
*A61K 39/00* (2006.01)
*C07K 16/18* (2006.01)

(52) U.S. Cl.
CPC .......... *A61K 39/0005* (2013.01); *A61K 35/15* (2013.01); *C07K 16/18* (2013.01); *A61K 2039/505* (2013.01); *A61K 2039/5154* (2013.01)

(58) Field of Classification Search
CPC ............ A61K 39/0005; A61K 39/0007; A61K 35/15; A61K 2039/5154
See application file for complete search history.

(56) References Cited

U.S. PATENT DOCUMENTS

| 2003/0166558 | A1 | 9/2003 | Frangione et al. | |
|---|---|---|---|---|
| 2006/0259986 | A1* | 11/2006 | Chilcote | A01K 67/0275 800/3 |
| 2009/0041792 | A1 | 2/2009 | Belardelli et al. | |
| 2010/0278814 | A1* | 11/2010 | Schenk | A61K 39/0007 424/133.1 |
| 2015/0232524 | A1* | 8/2015 | Agadjanyan | C07K 14/4711 424/185.1 |

FOREIGN PATENT DOCUMENTS

| WO | WO-200153457 A2 | 7/2001 |
|---|---|---|
| WO | WO-2008103472 A2 | 8/2008 |

OTHER PUBLICATIONS

Alves da Costa C. Recent advances on alpha-synuclein cell biology: Functions and dysfunctions. Curr. Mol. Med. 2003, 3:17-24. (Year: 2003).*
Cao C et al. Antigen-sensitized dendritic cell vaccine against human alpha-synuclein: A potential cell-based therapy against Parkinson's disease. Ann. Neurol. 2011, 70 (Suppl 15), p. S14, Abstract # S202, 136th Annual Meeting of the American Neurological Association, Sep 25, 2011. p. S4 also provided(Year: 2011).*
International Search Report dated Aug. 23, 2015 in International Application No. 2015032453.
Shahaduzzaman et at. "Anti-Human α-Synuclein N-Terminal Peptide Antibody Protects against Dopaminergic Cell Death and Ameliorates Behavioral Deficits in an AAV-α-Synuclein Rat Model of Parkinson's Disease," PLoS One journal, Feb. 6, 2015, pp. 1-16, vol. 10, No. 2, e0116841.
Ugen et al. "Evaluation of an α-synuclein sensitized dendritic cell based vaccine in a transgenic mouse model of Parkinson disease," Human Vaccines & Immunotherapeutics journal, Feb. 25, 2015, pp. 922-930, vol. 11, Issue 4.
Damier, P., et al., "The Substantia Nigra of the Human Brain II. Patterns of Loss of Dopamine-Containing Neurons in Parkinson's Disease." Brain, 1999, pp. 1437-1448, 122, Oxford University Press.
Bernheimer, H., et al., "Brain Dopamine and the Syndromes of Parkinson and Huntington." Journal of the Neurological Sciences, 1973, pp. 415-455, 20, Elsevier Scientific Publishing Company, Amsterdam, the Netherlands.
Spillantini, Maria Grazia, et al., "α-Synuclein in Filamentous Inclusions of Lewy Bodies from Parkinson's Disease and Dementia with Lewy Bodies." Proc. Natl. Acad. Sci. USA, May 1998, pp. 6469-6473, vol. 95.
Braak, H., et al., "Staging of the Intracerebral Inclusion Body Pathology Associated with Idiopathic Parkinson Disease (Preclinical and Clinical Stages)." J Neurol, 2002, [Suppl 3]:III/1-III/5, 249.
Brochard, Vanessa, et al., "Infiltration of CD4+ Lymphocytes into the Brain Contributes to Neurodegeneration in a Mouse Model of Parkinson Disease." J. Clin. Invest., 2009, pp. 182-192, 119.
Berardelli, A., et al., "Pathophysiology of Bradykinesia in Parkinson Disease." Brain, 2001, pp. 2131-2146, 124.
Tran, Hien T., et al., "α-Synuclein Immunotherapy Blocks Uptake and Tem plated Propagation of Misfolded α-Synuclein and Neurodegeneration." Cell Reports, Jun. 26, 2014, pp. 2054-2065, 7.
Masliah, Eliezer, et al., "Passive Immunization Reduces Behavioral and Neuropathological Deficits in an α-Synuclein Transgenic Model of Lewy Body Disease." PLoS One, Apr. 2011, pp. 1 -17, vol. 6, Issue 4, e19338.

(Continued)

*Primary Examiner* — Kimberly Ballard
(74) *Attorney, Agent, or Firm* — Saliwanchik, Lloyd & Eisenschenk

(57) ABSTRACT

The present invention pertains to a dendritic cell-based vaccine against rh-α-Syn, α-synuclein specific peptide antibodies and related vaccines, and methods of treating, preventing, and/or vaccinating against Parkinson's Disease (PD), or symptoms thereof.

15 Claims, 14 Drawing Sheets
Specification includes a Sequence Listing.

(56) References Cited

OTHER PUBLICATIONS

Games, Dora, et, al., "Reducing C-Terminal-Truncated Alpha-Synuclein by Immunotherapy Attenuates Neurodegeneration and Propagation in Parkinson Disease-Like Models." The Journal of Neuroscience, Jul. 9, 2014, pp. 9441-9454, 34, 28.
Schneeberger, A., et al., "Vaccination for Parkinson Disease." Parkinsonism and Related Disorders, 2012, S11-S13, 18 Suppl 1.
Sanchez-Guajardo, Vanesa, PHD, et al., "α-Synuclein Vaccination Prevents the Accumulation of Parkinson Disease-Like Pathologic Inclusions in Striatum in Association with Regulatory T Cell Recruitment in a Rat Model." J Neuropathol Exp Neurol, Jul. 2013; pp. 624-645, vol. 72, No. 7, The American Association of Neuropatholrogists, Inc.
Mougenot, Anne-Laure J., et al., "Production of a Monoclonal Antibody, Against Human α-Synuclein, in a Subpopulation of C57BL/6J Mice, Presenting a Deletion of the α-Synuclein Locus." Journal of Neuroscience Methods, 2010, pp. 268-276, 192, Elsevier B.V.
Masliah, Eliezer, et al. "Effects of α-Synuclein Immunization in a Mouse Model of Parkinson Disease." Neuron, Jun. 16, 2005, pp. 857-868, vol. 46, Elsevier, Inc.
Hirsch, Etienne, et al., "Monoclonal Antibodies Raised against Lewy Bodies in Brains from Subjects with Parkinson Disease." Brain Research, 1985, pp. 374-378, 345, Elsevier Science Publishers B.V. (Biomedical Division).
Banchereau, Jacques, et al., "Dendritic Cells and the Control of Immunity." Nature, Mar. 19, 1998, pp. 245-252, vol. 392, Macmillan Publishers Ltd.
Steinman, Ralph M. "The Dendritic Cell System and Its Role in Immunogenicity." Annual Rev Immunol, 1991, pp. 271-296, 9, Annual Reviews Inc.
Dubois, Bertrand, et al., "Dendritic cells directly modulate B cell growth and differentiation." Journal of Leukocyte Biology, Aug. 1999, pp. 224-230, vol. 66.
Dubois, Bertrand, et al., "Dendritic Cells Enhance Growth and Differentiation of CD40-Activated B Lymphocytes." J. Exp. Med., Mar. 3, 1997, pp. 941-951, vol. 185, No. 5, The Rockefeller University Press.
Fayette, Jérôme, et al., "Human Dendritic Cells Skew Isotype Switching of CD40-Activated Naive B Cells towards $IgA_1$ and $IgA_2$." J. Exp. Med., Jun. 2, 1997, pp. 1909-1918, vol. 185, No. 11, The Rockefeller University Press.
Clark, Edward A. "Regulation of B Lymphocytes by Dendritic Cells." J. Exp. Med., Mar. 3, 1997, pp. 801-803, vol. 185, No. 5, The Rockefeller University Press.
Barrou, Benoît, et al., "Vaccination of Prostatectomized Prostate Cancer Patients in Biochemical Relapse, with Autologous Dendritic Cells Pulsed with Recombinant Human PSA." Cancer Immunol Immunother, 2004, pp. 453-460, 53, Springer-Verlag.
Cohen, Sharon, et al., "B-Cell Lymphoma and Myeloma Protection Induced by Idiotype Vaccination with Dendritic Cells is Mediated Entirely by T Cells in Mice." J Immunother, 2005, pp. 461-466, vol. 28, No. 5, Lippincott Williams & Wilkins.
Gajewski, Thomas F. et al., "Immunization of HLA-A2+ Melanoma Patients with MAGE-3 or MelanA Peptide-Pulsed Autologous Peripheral Blood Mononuclear Cells Plus Recombinant Human Interleukin 12." Clinical Cancer Research, Mar. 2001, pp. 895s-901s, vol. 7.
Loveland, Bruce E., et al., "Mannan-MUC1-Pulsed Dendritic Cell Immunotherapy: A Phase I Trial in Patients with Adenocarcinoma." Clin Cancer Res, Feb. 1, 2006, pp. 869-877, 12, 3.
Mittendorf, Elizabeth A., M.D., et al., "Evaluation of the HER2/neu-Derived Peptide GP2 for Use in a Peptide-Based Breast Cancer Vaccine Trial." Cancer, Jun. 1, 2006, pp. 2309-2317, vol. 106, No. 11, America Cancer Society.
Satthaporn, S., et al., "Dendritic Cells (II): Role and Therapeutic Implications in Cancer." J.R. Coll. Surg. Edinb., Jun. 2001, pp. 159-167, 46.

Ide, Fuyuaki, et al., "Peptide-Loaded Dendritic-Cell Vaccination Followed by Treatment Interruption for Chronic HIV-1 Infection: A Phase 1 Trial." Journal of Medical Virology, 2006, pp. 711-718, 78, Wiley-Liss, Inc.
Pellegatta, S., et al., "Dendritic Cells Pulsed with Glioma Lysates Induce Immunity against Syngeneic Intracranial Gliomas and Increase Survival of Tumor-Bearing Mice." Neurological Research, Jul. 2006, pp. 527-531, vol. 28, W. S. Money & Son Ltd.
Cao, Chuanhai et al., "Mutant Amyloid-Beta-Sensitized Dendritic Cells as Alzheimer Disease Vaccine." Journal of Neuroimmunology, 2008, pp. 1-10, 200, Elsevier B.V.
Luo, Zhongqui et al., "Efficacy of a Therapeutic Vaccine Using Mutated β-Amyloid Sensitized Dendritic Cells in Alzheimer's Mice." J Neuroimmune Pharmacol, 2012, pp. 640-655, 7, Springer Science+Business Media, LLC.
Nabar, Neel R. et al., "Cell Therapy: a Safe and Efficacious Therapeutic Treatment for Alzheimer's Disease in APP+PSI Mice." PloS One, Dec. 2012, pp. 1-17, 7, 12, e49468.
Wesley, Johnna et al., "An Overview of Sipuleucel-T: Autologous Cellular Immunotherapy for Prostate Cancer." Human Vaccines & Immunotherapeutics, Apr. 2012, pp. 520-527, vol. 8, Issue 4, Landes Bioscience.
Small, Eric J. et al., "Immunotherapy of Hormone-Refractory Prostate Cancer with Antigen-Loaded Dendritic Cells." Journal of Clinical Oncology, Dec. 1, 2000, pp. 3894-3903, 18, 23, American Society of Clinical Oncology.
Sims, Robert B. "Development of Sipuleucel-T: Autologous Cellular Immunotherapy for the Treatment of Metastatic Castrate Resistant Prostate Cancer." Vaccine, 2012, pp. 4394-4397, 30, Elsevier Ltd.
Hart, Derek N.J. "Dendritic Cells: Unique Leukocyte Populations Which Control the Primary Immune Response." Blood, Nov. 1, 1997, pp. 3245-3287, 90, 9, The American Society of Hematology.
Steinman, Ralph M. "Dendritic Cells and the Control of Immunity: Enhancing the Efficiency of Antigen Presentation." The Mount Sinai Journal of Medicine, May 2001, pp. 160-166, vol. 68, No. 3, New York.
Shaftel, Solomon S., et al., "The Role of Interleukin-1 in Neuroinflammation and Alzheimer Disease: an Evolving Perspective." Journal of Neuroinflammation, 2008, 5, 7.
Hirsch, Etienne C. et al., "Neuroinflammation in Parkinson's Disease: a Target for Neuroprotection?" Lancet Neurol, Apr. 2009, pp. 382-397, vol. 8.
Basu, Anirban, et al., "Interleukin-1: a Master Regulator of Neuroinflammation." Journal of Neuroscience Research, 2004, pp. 151-156, 78, Wiley-Liss, Inc.
Fernagut, Pierre-Olivier et al., "Alpha-Synuclein and Transgenic Mouse Models." Neurobiology of Disease, 2004, pp. 123-130, 17, Elsevier Inc.
Morgan, Dave et al., "Aβ Peptide Vaccination Prevents Memory Loss in an Animal Model of Alzheimer's Disease." Nature, Dec. 2000, pp. 982-985, vol. 408, Macmillan Magazines Ltd.
McLaurin, J. et al., "Therapeutically Effective Antibodies Against Amyloid-β Peptide Target Amyloid-β Residues 4-10 and Inhibit Cytotoxicity and Fibrillogenesis." Nature Medicine, Nov. 2002, pp. 1263-1269, vol. 8, No. 11, Nature Publishing Group.
Cicin-Sain, Luka et al., "Loss of Naive T Cells and Repertoire Constriction Predict Poor Response to Vaccination in Old Primates." The Journal of Immunology, 2010, pp. 6739-6745, 184, The American Association of Immunologists, Inc., Bethesda, MD.
Sela, Michael et al., "Therapeutic Vaccines: Realities of Today and Hopes for the Future." DDT, Jun. 2002, pp. 664-673, vol. 7, No. 12, Elsevier Science Ltd.
Masliah, Eliezer et al., "Effects of α-Synuclein Immunization in a Mouse Model of Parkinson's Disease." Neuron, Jun. 16, 2005, pp. 857-868, vol. 46, Elsevier Inc.
Bachy, Véronique et al., "Mouse Vaccination with Dendritic Cells Loaded with Prion Protein Peptides Overcomes Tolerance and Delays Scrapie." Journal of General Virology, 2010, pp. 809-820, 91, SGM, Great Britain.
Okano, Fumiyoshi et al., "In Vivo Manipulation of Dendritic Cells Overcomes Tolerance to Unmodified Tumor-Associated Self Antigens and Induces Potent Antitumor Immunity." The Journal of

(56) References Cited

OTHER PUBLICATIONS

Immunology, 2005, pp. 2645-2652, 174, The American Association of Immunologists, Bethesda, MD.
Farag, Mohamed M.S. et al., "Immune Tolerance against HBV Can Be Overcome in HBV Transgenic Mice by Immunization with Dendritic cells Pulsed by HBVsvp." Vaccine, 2012, pp. 6034-6039, 30, Elsevier Ltd.
Yu, John S. et al., "Vaccination with Tumor Lysate-Pulsed Dendritic Cells Elicits Antigen-Specific, Cytotoxic T-Cells in Patients with Malignant Glioma." Cancer Research, Jul. 15, 2004, pp. 4973-4979, 64.
Nair, Smita K. et al., "Induction of Cytotoxic T Cell Responses and Tumor Immunity against Unrelated Tumors Using Telomerase Reverse Transcriptase RNA Transfected Dendritic Cells." Nature Medicine, Sep. 2000, pp. 1011-1017, vol. 6, No. 8, Nature America Inc.
Gruber, Andreas et al., "Dendritic Cell-Based Vaccine Strategy against Human Immunodeficiency Virus Clade C: Skewing the Immune Response toward a Helper T Cell Type 2 Profile." Viral Immunology, 2007, pp. 160-169, vol. 20, No. 1, Mary Ann Liebert, Inc.
Boscardin, Silvia B. et al., "Antigen Targeting to Dendritic Cells Elicits Long-Lived T Cell Help for Antibody Responses." The Journal of Experimental Medicine, Mar. 20, 2006, pp. 599-606, vol. 203, No. 3, The Rockefeller University Press.
Ikeda, Satoshi et al., "Excess IL-1 Signaling Enhances the Development of Th17 Cells by Downregulating TGF-β-Induced Foxp3 Expression." The Journal of Immunology, 2014, pp. 1449-1458, 192, The American Association of Immunologists, Inc., Bethesda, MD.
Noack, Mélissa et al., "Th17 and Regulatory T Cell Balance in Autoimmune and Inflammatory Diseases." Autoimmunity Reviews, 2014, pp. 668-677, 13, Elsevier B.V.
Giasson, Benoit I. et al., "Neuronal α-Synucleinopathy with Severe Movement Disorder in Mice Expressing A53T Human α-Synuclein." Neuron, May 16, 2002, pp. 521-533, vol. 34, Cell Press.
Rozas, G. et al., "An Automated Rotarod Method for Quantitative Drug-Free Evaluation of Overall Motor Deficits in Rat Models of Parkinsonism." Brain Research Protocols, 1997, pp. 75-84, 2, Elsevier Science B.V.
Meredith, Gloria E., PhD et al., "Behavioral Models of Parkinson's Disease in Rodents: a New Look at an Old Problem." Movement Disorders, 2006, pp. 1595-1606, vol. 21, No. 10, Movement Disorder Society.
Cao, Chuanhai et al., "Successful Adjuvant-Free Vaccination of BALB/c Mice with Mutated Amyloid β Peptides." BMC Neuroscience, 2008, 25, 9, Cao et al, licensee Biomed Central Ltd.
Alerte, T. N. M., et al., α-Synuclein aggregation alters tyrosine hydroxylase phosphorylation and immunoreactivity: Lessons from viral transduction of knockout mice, Neuroscience Letters, 2008, 435:24-29, Elsevier Ireland Ltd.
Anderson, N. L., et al., SISCAPA Peptide Enrichment on Magnetic Beads Using an In-line Bead Trap Device, Molecular & Cellular Proteomics 8.5, 2009, 8:995-1005, MCP Papers in Press, The American Society for Biochemistry and Molecular Biology, Inc.
Bae, E.-J., et al., Antibody-Aided Clearance of Extracellular α-Synuclein Prevents Cell-to-Cell Aggregate Transmission, The Journal of Neuroscience, Sep. 26, 2012, 32(39):13454-13469.
Bartels, T., et al., The N-Terminus of the Intrinsically Disordered Protein α-Synuclein Triggers Membrane Binding and Helix Folding, Biophysical Journal, Oct. 2010, 99(7):2116-2124, The Biophysical Society.
Boche, D., et al., Consequence of Aβ immunization on the vasculature of human Alzheimer's disease brain, Brain, 2008, 131:3299-3310, Oxford University Press on behalf of the Guarantors of Brain.
Boche, D., et al., Neuropathology after active Aβ42 immunotherapy: implications for Alzheimer's disease pathogenesis, Acta Neuropathologica, 2010, 120:369-384, Springer-Verlag.
Carty, N., et al., Convection-enhanced delivery and systemic mannitol increase gene product distribution of AAV vectors 5, 8, and 9 and increase gene product in the adult mouse brain, Journal of Neuroscience Methods, 2010, 194:144-153, Elsevier B.V.
Cribbs, D. H., et al., Adjuvant-dependent modulation of $T_h1$ and $T_h2$ responses to immunization with β-amyloid, International Immunology, 2003, 15(4):505-514, The Japanese Society for Immunology.
Decressac, M., et al., α-Synuclein-Induced Down-Regulation of Nurr1 Disrupts GDNF Signaling in Nigral Dopamine Neurons, Science Translational Medicine, Dec. 5, 2012, 4(163)163ra156:1-15, the American Association for the Advancement of Science, Washington DC.
Fagerqvist, T. et al., Monoclonal antibodies selective for α-synuclein oligomers/protofibrils recognize brain pathology in Lewy body disorders and α-synuclein transgenic mice with the disease-causing A30P mutation, Journal of Neurochemistry, 2013, 126:131-144, International Society for Neurochemistry.
Foulds, P. G., et al., Phosphorylated α-synuclein can be detected in blood plasma and is potentially a useful biomarker for Parkinson's disease, The Federation of American Societies for Experimental Biology Journal, Dec. 2011, 25(12):4127-4137, The Federation of American Societies for Experimental Biology.
Gardai, S. J., et al., Elevated Alpha-Synuclein Impairs Innate Immune Cell Function and Provides a Potential Peripheral Biomarker for Parkinson's Disease, PLoS ONE, Aug. 23, 2013, 8(8)e71634:1-21.
Ghochikyan, A., et al., Immunogenicity of epitope vaccines targeting different B cell antigenic determinants of human α-synuclein: Feasibility study, Neuroscience Letters, 2014, 560:86-91, Elsevier Ireland Ltd.
Gorbatyuk, O. S., et al., The phosphorylation state of Ser-129 in human α-synuclein determines neurodegeneration in a rat model of Parkinson disease, Proceedings of the National Academy of Sciences, Jan. 15, 2008, 105(2):763-768, The National Academy of Sciences of the USA.
Gorbatyuk, O. S., et al., α-Synuclein Expression in Rat Substantia Nigra Suppresses Phospholipase D2 Toxicity and Nigral Neurodegeneration, Molecular Therapy, Oct. 2010, 18(10):1758-1768, The American Society of Gene & Cell Therapy.
Harms, A. S., et al., MHCII Is Required for α-Synuclein-Induced Activation of Microglia, CD4 T Cell Proliferation, and Dopaminergic Neurodegeneration, The Journal of Neuroscience, Jun. 5, 2013, 33(23):9592-9600.
Uéda, K., et al., Molecular cloning of cDNA encoding an unrecognized component of amyloid in Alzheimer disease, Proceedings of the National Academy of Sciences USA, Dec. 1993, 90:11282-11286.
Holmes, C., et al., Long-term effects of $A\beta_{42}$ immunisation in Alzheimer's disease: follow-up of a randomised, placebo-controlled phase I trial, Lancet, Jul. 19, 2008, 372:216-223.
Iancu, R., et al., Behavioral characterization of a unilateral 6-OHDA-lesion model of Parkinson's disease in mice, Behavioural Brain Research, 2005, 162:1-10, Elsevier B. V.
Kim, T. D., et al., Structural and Functional Implications of C-Terminal Regions of α-Synuclein, Biochemistry, 2002, 41(46):13782-13790, American Chemical Society.
Kirik, D., et al., Reversal of motor impairments in parkinsonian rats by continuous intrastriatal delivery of $_L$-dopa using rAAV-mediated gene transfer, Proceedings of the National Academy of Sciences, Apr. 2, 2002, 99(7):4708-4713.
Kortekaas, R., et al., Blood-Brain Barrier Dysfunction in Parkinsonian Midbrain In Vivo, Annals of Neurology, 2005, 57:176-179, Wiley-Liss, Inc, American Neurological Association.
Kosloski, L. M., et al., Adaptive immune regulation of glial homeostasis as an immunization strategy for neurodegenerative diseases, Journal of Neurochemistry, 2010, 114:1261-1276, International Society for Neurochemistry.
Kothawala, A., et al., Quantitative Analysis of α-Synuclein Solubility in Living Cells Using Split GFP Complementation, PLoS ONE, Aug. 22, 2012, 7(8)e43505:1-9.
Lambracht-Washington, D., et al., Anti-amyloid-beta to tau-based immunization: developments in immunotherapy for Alzheimer's disease, ImmunoTargets and Therapy, 2013, 2:105-114, Dove Medical Press Ltd.

(56) References Cited

OTHER PUBLICATIONS

Lannfelt, L., et al., Perspectives on future Alzheimer therapies: amyloid-β protofibrils—a new target for immunotherapy with BAN2401 in Alzheimer's disease, Alzheimer's Research & Therapy, 2014, 6(16):1-8, BioMed Central Ltd.

Lashuel, H. A., et al., The many faces of α-synuclein: from structure and toxicity to therapeutic target, Nature Reviews, Jan. 2013, 14:38-48, Macmillan Publishers Limited.

Lemere, C. A. Immunotherapy for Alzheimer's disease: hoops and hurdles, Molecular Neurodegeneration, 2013, 8(36):1-6, BioMed Central Ltd.

Lindström, V., et al., Immunotherapy targeting α-synuclein protofibrils reduced pathology in (Thy-1)-h[A30P] α-synuclein mice, Neurobiology of Disease, 2014, 69:134-143, Elsevier Inc.

Lundblad, M., et al., Pharmacological validation of behavioural measures of akinesia and dyskinesia in a rat model of Parkinson's disease, European Journal of Neuroscience, 2002, 15:120-132, Federation of European Neuroscience Societies.

Mandler, M., et al., Next-generation active immunization approach for synucleinopathies: implications for Parkinson's disease clinical trials, Acta Neuropathologica, 2014, 127:861-879, Springer-Verlag Berlin Heidelberg.

Marciniuk, K. et al., Evidence for Prion-Like Mechanisms in Several Neurodegenerative Diseases: Potential Implications for Immunotherapy, Clinical and Developmental Immunology, 2013, 2013(473706):1-20, Hindawi Publishing Corporation.

Mathews, P. M., et al., Setback for an Alzheimer's disease vaccine Lessons learned, Neurology, Jul. 2003, 61:7-8, AAN Enterprises, Inc.

McLean, P. J., et al., Membrane Association and Protein Conformation of α-Synuclein in Intact Neurons, Effect of Parkinson's Disease-Linked Mutations, The Journal of Biological Chemistry, Mar. 24, 2000, 275(12):8812-8816, The American Society for Biochemistry and Molecular Biology, Inc., USA.

Madeo, J., et al., Alzheimer's Disease and Immunotherapy, Aging and Disease, Aug. 2013, 4(4):210-220.

Mosley, R. L., et al., Inflammation and Adaptive Immunity in Parkinson's Disease, Cold Spring Harbor Perspectives in Medicine, 2012, 2(a009381):1-17, Cold Spring Harbor Laboratory Press.

Narhi, L., et al., Both Familial Parkinson's Disease Mutations Accelerate α-Synuclein Aggregation, The Journal of Biological Chemistry, Apr. 2, 1999, 274(14):9843-9846, The American Society for Biochemistry and Molecular Biology, Inc., USA.

Orgogozo, J.-M., et al., Subacute meningoencephalitis in a subset of patients with AD after Aβ42 immunization, Neurology, Jul. 2003, 61:46-54, AAN Enterprises, Inc.

Pabon, M. M., et al., A Spirulina-Enhanced Diet Provides Neuroprotection in an α-Synuclein Model of Parkinson's Disease, PLoS ONE, Sep. 2012, 7(9)e45256:1-7.

Peterson, R. A., Regulatory T-Cells: Diverse Phenotypes Integral to Immune Homeostasis and Suppression, Toxicologic Pathology, 2012, 40(2):186-204.

Schallert, T., et al., Experience-Associated Structural Events, Subependymal Cellular Proliferative Activity, and Functional Recovery After Injury to the Central Nervous System, Journal of Cerebral Blood Flow and Metabolism, 2000, 20(11):1513-1528, Lippincott Williams & Wilkins, Inc., The International Society for Cerebral Blood Flow and Metabolism, Philadelphia.

Shaw, A. C., et al., Aging of the innate immune system, Current Opinion in Immunology, 2010, 22:507-513, Elsevier Ltd.

Stefanis, L., α-Synuclein in Parkinson's Disease, Cold Spring Harbor Perspectives in Medicine, 2012, 4(a009399):1-23, Cold Spring Harbor Laboratory Press.

Valera, E., et al., Immunotherapy for neurodegenerative diseases: Focus on α-synucleinopathies, Pharmacology & Therapeutics, 2013, 138:311-322, Elsevier Inc.

Vamvaca, K., et al., The First N-terminal Amino Acids of α-Synuclein Are Essential for α-Helical Structure Formation In Vitro and Membrane Binding in Yeast, Journal of Molecular Biology, 2009, 389:413-424, Elsevier Ltd.

Weng, N.-P., Aging of the Immune System: How Much Can the Adaptive Immune System Adapt?, Immunity, May 2006, 24:495-499, Elsevier Inc.

Zhang, X., et al., Conformation-dependent scFv antibodies specifically recognize the oligomers assembled from various amyloids and show colocalization of amyloid fibrils with oligomers in patients with amyloidoses, Biochimica et Biophysica Acta, 2011, 1814:1703-1712, Elsevier B.V.

\* cited by examiner

B

| Genotype Group | TG Rx PS DC | WT control | TG non-Rx | TG hr-α-Syn DC |

β-actin

α-Syn

| Genotype Group | TG Rx PS DC | WT control | TG non-Rx | TG hr-α-Syn DC |

β-actin

α-Syn

SEQUENCE LISTING

<160> NUMBER OF SEQ ID NOS: 3

<210> SEQ ID NO 1
<211> LENGTH: 20
<212> TYPE: PRT
<213> ORGANISM: Homo sapiens

<400> SEQUENCE: 1

Val Ala Ala Ala Glu Lys Thr Lys Gln Gly Val Ala Glu Ala Ala Gly

```
1               5                10               15
Lys Thr Lys Glu
            20

<210> SEQ ID NO 2
<211> LENGTH: 23
<212> TYPE: PRT
<213> ORGANISM: Homo sapiens

<400> SEQUENCE: 2

Gly Phe Val Lys Lys Asp Gln Leu Gly Lys Asn Glu Glu Gly Ala Pro
1               5                   10                  15

Gln Glu Gly Ile Leu Glu Asp
            20

<210> SEQ ID NO 3
<211> LENGTH: 21
<212> TYPE: PRT
<213> ORGANISM: Homo sapiens

<400> SEQUENCE: 3

Met Pro Val Asp Pro Asp Asn Glu Ala Tyr Glu Met Pro Ser Glu Glu
1               5                   10                  15

Gly Tyr Gln Asp Tyr
            20
```

METHODS, ANTIBODIES, AND VACCINES UTILIZING EPITOPES OF ALPHA SYNUCLEIN FOR TREATMENT OF PARKINSONS DISEASE

CROSS-REFERENCE TO RELATED APPLICATIONS

This application is the U.S. national stage application of International Patent Application No. PCT/US2015/032453, filed May 26, 2015, which claims the benefit of U.S. provisional application Ser. No. 62/002,535, filed May 23, 2014, which are herein incorporated by reference in their entirety.

BACKGROUND

Parkinson's Disease (PD) is a neurodegenerative disease caused by progressive accumulation of abnormal intracellular aggregates of alpha synuclein (α-Syn) protein existing as Lewy bodies, the pathological hallmark of the disease. Lewy bodies first appear in the olfactory bulb and medulla and gradually spread to midbrain, at which time, the first motor signs of PD appear (Braak et al., 2002). Concomitantly, inflammatory responses from resident microglia result in T-cell recruitment, setting off an exacerbating inflammatory cascade (Brochard et al., 2009). Together, these events lead to the progressive demise of nigrostriatal dopaminergic neurons, resulting in the classical clinical signs of bradykinesia, rest tremor, and rigidity. Symptomatic relief is provided by dopamine replacement, but the underlying disease process continues unabated. The advances in research with immunotherapies for AD have opened new opportunities for treatment of PD. Vaccines developed against α-Syn protein and administration of antibodies against α-Syn have been studied by several research groups (Hirsch et al., 1985, Masliah et al., 2005, Mougenot et al., 2010).

Dendritic cells (DCs) play a central role in initiating the primary immune response, through antigen presentation to T cells (Steinman, 1991, Banchereau and Steinman, 1998). Moreover, recent studies have revealed that DCs can induce proliferation of B cells and directly stimulate production of antibodies (Dubois et al., 1997, Dubois et al., 1999). DCs also govern immunoglobulin class-switching, such as immunoglobulin A2 expression (Fayette et al., 1997) indicating that DCs regulate the humoral immune response as well, in part via a direct interaction with B cells (Clark, 1997).

Many immunotherapies have been developed since the first vaccine against Alzheimer's disease (AD) was published. Clinical trials have also been conducted by several companies, but there is no success yet. The vaccines and immunotherapies against neurodegenerative diseases have to be able to deal with the pathological protein as well as the impaired immune system, because age is the most important risk factor for such disease, and the immune system declines with aging.

Antigen-sensitized DCs have been used as vaccines in many fields (Gajewski et al., 2001, Satthaporn and Eremin, 2001, Barrou et al., 2004, Cohen et al., 2005, Loveland et al., 2006, Mittendorf et al., 2006). DC vaccines also have already been approved by the FDA for clinical use in various diseases, such as HIV and cancer (Ide et al., 2006, Pellegatta et al., 2006). DCs sensitized with mutant Aβ peptides were used to vaccinate a mouse model of AD, without eliciting a generalized inflammatory response (Cao et al., 2008).

SUMMARY OF THE INVENTION

The present invention provides a dendritic cell-based vaccine against α-synuclein, antibodies against α-synuclein, and methods of treating, preventing, and/or vaccinating against Parkinson's Disease (PD).

In one aspect, the present invention provides a vaccine composition comprising an isolated dendritic cell that is sensitized to at least one peptide fragment of the α-synuclein protein.

In another aspect, the present invention provides methods of treating symptoms of PD in a subject and/or vaccinating the subject against PD. The methods comprise administering an isolated dendritic cell to a subject in need thereof, wherein the dendritic cell is sensitized to at least one peptide fragment of the α-synuclein protein prior to administering to the subject.

In another aspect, the present invention provides methods of treating symptoms of PD in a subject and/or passively vaccinating the subject against PD. The methods comprise administering an anti-α-synuclein peptide antibody to a subject in need thereof.

In another aspect, the present invention provides methods of protecting against dopaminergic neuron cell death in a subject. The methods comprise administering an anti-α-synuclein peptide antibody to a subject in need thereof, whereby dopaminergic neurons are protected from cell death due to α-synuclein mediated neurodegeneration. In preferred embodiments, the anti-α-synuclein peptide antibody is specific for the N-terminal region of the α-synuclein protein. In some embodiments, the anti-α-synuclein peptide antibody is specific for a peptide with the peptide sequence of SEQ ID NO: 1.

In embodiments of aspects of the present invention, the at least one peptide fragment of the α-synuclein protein comprises an amino acid sequence selected from SEQ ID NO:1, SEQ ID NO:2, SEQ ID NO:3, and combinations thereof. Furthermore, in some embodiments the dendritic cell is autologous and may be obtained from the subject by leukapheresis. In some embodiments, the subject is a human subject.

The methods and compositions herein described can be used in connection with pharmaceutical, medical, and veterinary applications, as well as fundamental scientific research and methodologies, as would be identifiable by a skilled person upon reading of the present disclosure. These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying figures in which:

FIG. 4 (C) shows quantification of results of (B). There were no significant differences among treatment groups, and the α-Syn level from wild type can be considered as background.

BRIEF DESCRIPTION OF THE SEQUENCES

Figure 1:
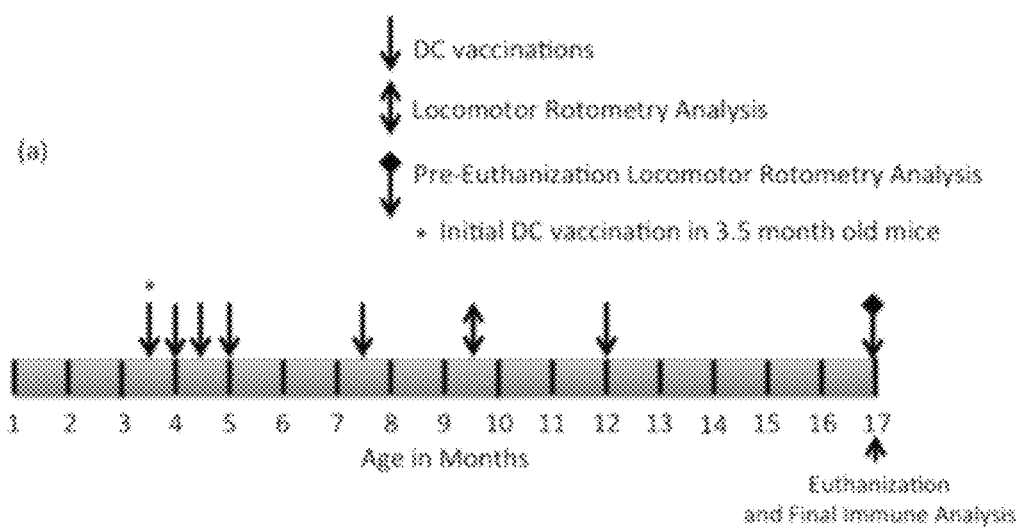
FIG. 1 shows an illustration of the vaccination and rotometry testing schedule and amino acid sequences of DC sensitizing peptides. (A) Schedule for vaccination, rotometry testing and euthanasia as described further in the materials and methods herein. The initial vaccination with sensitized or non-sensitized DCs was made in 3.5 month old α-synuclein (α-Syn) expressing Tg mice. (B) Amino acid sequence and residue numbers for the 3 α-Syn specific B cell epitope-containing peptides used as DC sensitizers: Peptide Fragment A (SEQ ID NO:1), Peptide Fragment B (SEQ ID NO:2) and Peptide Fragment C (SEQ ID NO:3).

SEQ ID NO: 1 is a peptide fragment of the human α-synuclein protein.
SEQ ID NO: 2 is a peptide fragment of the human α-synuclein protein.
SEQ ID NO: 3 is a peptide fragment of the human α-synuclein protein.

DETAILED DISCLOSURE OF THE INVENTION

Aggregates of the brain protein alpha-synuclein (α-Syn) are generally considered to have a major role in the pathological development and progression of (Parkinson's Disease) PD (Kothawala et al., 2012). Active or passive immunotherapy directed against misfolded proteins associated with neurodegenerative diseases such as α-Syn for PD (Lindstrom et al., 2014; Fagerqvist et al., 2013; Mandler et al., 2014) and amyloid beta (Aβ) for Alzheimer's disease (AD) therapy, have yielded promising results (Madeo, 2013; Lannfelt et al., 2014). A number of clinical trials on immunotherapies against Aβ are now under way (Lemere et al., 2010; Rafii, 2013). Several clinical studies have demonstrated the efficacy of immune-based approaches in lowering Aβ load in the brains of AD patients (Holmes et al., 2008; Boche et al., 2010). However, vaccine associated side effects such as meningoencephalitis and cerebral microhemorrhaging in the brains of some of the subjects in the Aβ vaccine trials have tempered the enthusiasm for this strategy (Boche et al., 2008; Lambracht-Washington et al., 2013; Orgogozo et al., 2003). Preclinical evidence has suggested that other misfolded proteins including hyperphosphorylated tau, prion proteins, huntington, TAR DNA-binding protein 43, and mutant superoxide dismutase 1 (SOD1) can also be targeted for immunotherapeutic strategies (Marciniuk et al., 2013). Evidence supporting immunotherapy against α-Syn as an experimental treatment option for PD comes from preclinical studies using different mouse models for PD (Schneeberger et al., 2012; Hutter-Saunders et al., 2011). Inhibition of α-Syn aggregation using small molecules, enhanced clearance of α-Syn through the lysosomal pathways, and decreased neuroinflammation are among the most prevalent therapeutic strategies being investigated (Stefanis, 2012). However, targeting intracellular α-Syn protein continues to be a major challenge for immunotherapy due to the presence of diverse forms (i.e. oligomeric and phosphorylated) detected in human plasma and CSF (Lashuel et al., 2013; Foulds et al., 2011). Despite the scientific progress using immunotherapy against other neurogdegenerative diseases, only one clinical trial (AFFI-TOPE PD01A, NCT01568099) based on immunotherapy has been approved for PD to date.

Structurally, human α-Syn is an intrinsically disordered 140 amino acid long protein consisting of three distinct regions: an N-terminal region (residues 1-60) which forms a helical structure and interacts with the cellular membrane (McLean et al., 2000), a central highly aggregation-prone non-Aβ component region (residues 61-95) (Ueda et al., 1993) and a C-terminal region (residues 96-140) that is highly enriched in acidic residues and prolines (Kim et al., 2002). It has been demonstrated that immunotherapy with an antibody targeted against the C-terminus of α-Syn promoted clearance of this protein from neuronal cells in an α-Syn expressing transgenic PD mouse model (Masliah et al., 2011). Other researchers have demonstrated that these antibodies can enter the brain and reduce both intracellular and extracellular levels of α-Syn (Vekrellis et al., 2012). To date, there have not been any studies evaluating the potential efficacy of antibodies directed against the N-terminal region of α-Syn. It has been demonstrated that all three mutations of α-Syn, A30P, E46K and A53T, occur within the N-terminal region and are associated with inherited early-onset variants of PD. These mutants are able to accelerate α-Syn oligomerization and protofibrilar aggregation of this protein (Narhi et al., 1999). Thus, the identification of the interaction sites within the N-terminal regions with specific antibodies may provide a novel immunotherapeutic approach against PD.

Age has been determined to be a major risk factor for neurodegenerative diseases, such as AD and PD. Of relevance as well is the observation that immune responses also decline with age, which may potentially have an important role in the pathophysiology of neurodegenerative diseases. Importantly, in both human and animal models of PD, α-Syn aggregation is accompanied by activation of both the innate and adaptive immune responses (Gardai et al., 2013; Mosley et al., 2012). These include increased microglial activation as evidenced by enhanced MHCII expression (Sanchez-Guajardo et al., 2013), altered serum IgG production, (Koehler et al., 2013) and infiltration of CD4 lymphocytes surrounding degenerating neurons (Brochard et al., 2009). Post-mortem studies of the brains of patients suffering from PD have consistently demonstrated microglial activation in the substantia nigra (SN). It has been proposed that activated microglia promote α-Syn aggregation by perpetuating pro-inflammatory immune responses in PD brains through the generation of reactive oxygen species (ROS) and many other soluble factors, including chemokines and cytokines such as TNF-α, NFκB1, IL-15, RANTES, and IL-10 (Peterson, 2012). This ultimately leads to further neurodegeneration. However, it has also been demonstrated that immune responses against α-Syn can mediate the removal of this protein, to varying extents, from the brain.

It has been reported previously that anti-α-Syn monoclonal antibodies directed against the C-terminal of α-Syn enhanced the clearing of intracellular α-Syn aggregates (Masliah et al., 2011; Bae et al., 2012). Recently, a monoclonal antibody (Syn303) directed against N-terminus of α-synuclein (amino acids 1-5) reduced propagation of synuclein fibrils in the ipsilateral frontal cortex, SNpc, and the amygdala (Tran et al., 2014). The present invention determines the potential protective effects of passive immunotherapy with an anti-α-Syn antibody directed against the N-terminus or central region of α-Syn. In contrast to active vaccination, passive immunotherapy has been demonstrated to have a regulatory effect on microglial equilibrium and may be a safer alternative to active immunization (Kosloski et al., 2010). The antibodies of the present invention confer neural protection and ameliorate behavioral deficits by reducing the levels of α-Syn. The present invention also investigates the effects of the generated antibodies on PD-associated immune response impairment, notably on microglial homeostasis. It was determined that the antibody treatments evaluated considerably reduce the number of activated microglia, therefore preventing the progressive loss of DA from α-Syn mediated toxicity. From these results it is concluded that passive immunotherapy against the N-terminus of α-Syn is a valid and useful therapeutic strategy against PD.

Several aspects of the invention are described below, with reference to examples for illustrative purposes only. It should be understood that numerous specific details, relationships, and methods are set forth to provide a full understanding of the invention. One having ordinary skill in the relevant art, however, will readily recognize that the invention can be practiced without one or more of the specific details or practiced with other methods, protocols, reagents, cell lines and animals. The present invention is not limited by the illustrated ordering of acts or events, as some acts may occur in different orders and/or concurrently with other acts or events. Furthermore, not all illustrated acts, steps or events are required to implement a methodology in accordance with the present invention. Many of the techniques and procedures described, or referenced herein, are well understood and commonly employed using conventional methodology by those skilled in the art.

Prior to setting forth the invention in detail, it may be helpful to the understanding thereof to define several terms, and these are accordingly set forth in the next section, below. Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. It will be further understood that terms, such as those defined in commonly used dictionaries, should be interpreted as having a meaning that is consistent with their meaning in the context of the relevant art and/or as otherwise defined herein.

Definitions

The terminology used herein is for the purpose of describing particular embodiments only and is not intended to be limiting of the invention. As used herein, the indefinite articles "a", "an" and "the" should be understood to include plural reference unless the context clearly indicates otherwise.

The phrase "and/or," as used herein, should be understood to mean "either or both" of the elements so conjoined, i.e., elements that are conjunctively present in some cases and disjunctively present in other cases.

As used herein, "or" should be understood to have the same meaning as "and/or" as defined above. For example, when separating a listing of items, "and/or" or "or" shall be interpreted as being inclusive, i.e., the inclusion of at least one, but also including more than one, of a number of items, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

As used herein, the terms "including", "includes", "having", "has", "with", or variants thereof, are intended to be inclusive similar to the term "comprising."

As used herein, the term "subject" refers to an animal. Typically, the terms "subject" and "patient" may be used interchangeably herein in reference to a subject. As such, a "subject" includes an animal that is being treated for a disease, being immunized, or the recipient of a mixture of components as described herein, such as a vaccine. The term "animal," includes, but is not limited to, mouse, rat, dog, guinea pig, cow, horse, chicken, cat, rabbit, pig, monkey, chimpanzee, and human.

As used herein, the term "vaccine" or "immunizing formulation" refers to any composition that stimulates an immune response to a particular antigen or antigens. Thus, a vaccine refers to any composition that is administered to a subject with the goal of establishing an immune response and/or immune memory to a particular antigen. It is also contemplated that the vaccine compositions can comprise other substances designed to increase the ability of the vaccine to generate an immune response. It is also contemplated that the vaccines disclosed herein can be therapeutic or prophylactic. Thus, for example, the vaccines disclosed herein can be used to prevent a disease, such as Parkinson's Disease (PD). Alternatively, the vaccines disclosed herein can be used therapeutically to treat an individual with PD or an individual having symptoms of PD.

The vaccines, compositions, and related methods of the present invention are utilized for treatment of symptoms related to PD-induced disabilities that are clinically observable, as well as the degeneration of neurons. The treatments can result in inhibition of or slowing of PD-induced neurodegeneration.

In one aspect, the present invention provides an antigen sensitized dendritic cell (DC) vaccine and related methods of vaccination utilizing the antigen sensitized DCs. In some embodiments, more than one antigen sensitized DC is utilized in the mixtures of compositions herein disclosed. For example, a mixture can comprise one or more dendritic cell sensitized to a peptide of a protein and a second one or more dendritic cell sensitized to another peptide of the same, or related, protein.

In another aspect, the present invention provides compositions comprising one or more peptides having sequences of SEQ ID NOs: 1, 2, or 3 and related methods of utilizing the peptide compositions for generation of antibodies for passive vaccination. For example, the peptides (of human origin) are administered as antigens to a non-human subject, such as e.g., a mouse. When the vaccine is administered to a non-human subject, the resultant antibodies generated may be utilized in a passive vaccination in a human subject.

The disclosed methods can comprise the simultaneous or separate administration of multiple vaccines. Thus, the present invention further includes the administration of a second, third, fourth, etc. vaccine (containing one or more antigen sensitized DCs, peptides, antibodies, or combinations thereof) wherein the second, third, fourth, etc. vaccine (containing one or more antigen sensitized DCs, peptides, antibodies, or combinations thereof) is administered in a separate vaccine for administration at the same time as or 1, 2, 3, 4, 5, 6, 10, 14, 18, 21, 30, 60, 90, 120, 180, 360 days (or any number of days in between) after the first vaccine (containing one or more antigen sensitized DCs, peptides, antibodies, or combinations thereof).

The term "pharmaceutically acceptable," as used herein with regard to compositions and formulations, means approved by a regulatory agency of the Federal or a state government or listed in the U.S. Pharmacopeia or other generally recognized pharmacopeia for use in animals and/or in humans.

The term "carrier" refers to a diluent, excipient, and/or vehicle with which the compositions, antibodies, and vaccines described herein are administered. Such pharmaceutical carriers can be sterile liquids, such as water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. Suitable pharmaceutical excipients include, but are not limited to, starch, glucose, sucrose, gelatin, lactose, malt, rice, flour, chalk, silica gel, sodium stearate, glycerol monostearate, talc, sodium chloride, glycerol, propylene, glycol, water, ethanol and the like. The compositions and formulations described herein may also contain wetting or emulsifying agents or suspending/diluting agents, or pH buffering agents, or agents for modifying or maintaining the rate of release of the composition. Formulations can include standard carriers such as pharmaceutical grades of mannitol, lactose, sodium saccharine, starch, magnesium stearate, cellulose, magnesium carbonate, etc. Such compositions and vaccines will contain an effective amount of the one or more antibodies, peptide antigen(s), and/or sensitized dendritic cell(s) (DCs) together with a suitable amount of carrier so as to provide the proper form to the patient based on the mode of administration to be used.

If for intravenous administration, the vaccines and compositions and antibodies can be packaged in solutions of sterile isotonic aqueous buffer. Where necessary, the vaccines and compositions and antibodies may also include a solubilizing agent. The components of the composition are supplied either separately or mixed together in unit dosage form. If the composition is to be administered by infusion, it can be dispensed with an infusion bottle containing sterile pharmaceutical grade water or saline. Where the composition is administered by injection, an ampoule of sterile water or saline can be provided so that the ingredients may be mixed prior to injection.

One aspect of the present invention provides a dendritic cell-based vaccine against α-Syn and methods of treating, preventing, and/or vaccinating against Parkinson's Disease (PD). Dendritic cell (DC) vaccination is a cell-based therapy that elicits an immune response by using antigen-loaded DCs as the vehicle for immunization. This is one of many experimental approaches to PD treatment, and could be among the leading therapeutic options for PD with additional development. An important advantage is that dendritic cells act as their own adjuvant to elicit an immune response (Hart, 1997). DCs loaded with peptide directly interact with the immune system without eliciting generalized inflammation that typically occurs in adjuvant-containing vaccines. Moreover, peptide-sensitized DC (PSDC) vaccines trigger a longer lasting antigen-specific T cell response unlike the shorter responses to traditional vaccines (Steinman, 2001). Despite the fact that PSDC vaccination has many advantages, this approach has never been explored in a PD-related study. The present invention, in certain embodiments, provides rh-α-Syn and α-Syn peptides for sensitizing DCs to test the effects of vaccination on the immune response in a Tg mouse model of PD that expresses human A53T variant α-Syn (B6; C3-Tg(Prnp-SNCA*A53T)83Vle/J) (full-length, 140 amino acid isoform) under the direction of the mouse prion protein promoter.

In one aspect, the present invention provides methods of treating symptoms of PD, such as, e.g., neurodegeneration, in a subject and/or vaccinating the subject against PD. The methods comprise administering an isolated dendritic cell to a subject in need thereof, wherein the dendritic cell is sensitized to at least one peptide fragment of the α-synuclein protein prior to administering to the subject.

In one aspect, the present invention provides methods of inhibition of neurodegeneration, such as PD-induced neurodegeneration, in a subject and/or vaccinating the subject against PD-induced neurodegeneration. The methods comprise administering an isolated dendritic cell to a subject in need thereof, wherein the dendritic cell is sensitized to at least one peptide fragment of the α-synuclein protein prior to administering to the subject.

In another aspect, the present invention provides a vaccine composition comprising an isolated dendritic cell that is sensitized to at least one peptide fragment of the α-synuclein protein. In at least one embodiment, the vaccine composition further comprises at least one pharmaceutically acceptable carrier.

In another aspect, the present invention provides a vaccine composition comprising an anti-α-synuclein peptide antibody. In at least one embodiment, the vaccine composition further comprises at least one pharmaceutically acceptable carrier.

In another aspect, the present invention provides an anti-α-synuclein peptide antibody that is specific for the amino acid sequence of SEQ ID NO:1, or a fragment thereof.

In another aspect, the present invention provides an anti-α-synuclein peptide antibody that is specific for the amino acid sequence of SEQ ID NO:2, or a fragment thereof.

In another aspect, the present invention provides an anti-α-synuclein peptide antibody that is specific for the amino acid sequence of SEQ ID NO:3, or a fragment thereof.

In some embodiments, the anti-α-synuclein peptide antibodies of the present invention are isolated antibodies.

In another aspect, the present invention provides a vaccine composition comprising at least one peptide fragment of an α-synuclein protein comprising the sequence of SEQ ID NO: 1, SEQ ID NO: 2, or SEQ ID NO: 3. In some embodiments, the least one peptide fragment of an α-synuclein protein comprises one or more fragment of the sequence of SEQ ID NO: 1, SEQ ID NO: 2, or SEQ ID NO: 3. In at least one embodiment, the vaccine composition further comprises at least one pharmaceutically acceptable carrier.

In another aspect, the present invention provides methods of passive vaccination for PD or symptoms thereof utilizing antibodies to at least one peptide fragment of an α-synuclein protein comprising the sequence of SEQ ID NO: 1, SEQ ID NO: 2, or SEQ ID NO: 3. The methods comprise administered at least one peptide fragment of an α-synuclein protein comprising the sequence of SEQ ID NO: 1, SEQ ID NO: 2, or SEQ ID NO: 3 to a non-human subject, such as e.g., a mouse; isolating the resultant antibodies generated against the at least one peptide fragment of the α-synuclein protein; and administering the resultant antibodies to a human subject.

In embodiments of aspects of the present invention, the at least one peptide fragment of the α-synuclein protein comprises an amino acid sequence selected from SEQ ID NO:1, SEQ ID NO:2, SEQ ID NO:3, and combinations thereof. As would be understood by those skilled in the art, amino acid sequences selected from SEQ ID NO:1, SEQ ID NO:2, SEQ ID NO:3 can also be utilized in embodiments of the present invention which contain point mutations (e.g., missense mutations and silent mutations) or peptide deletions, as long as the resulting antibody maintains recognition and binding of the native α-synuclein protein.

In one embodiment, at least one peptide fragment of the α-synuclein protein comprises an amino acid sequence consisting of SEQ ID NO:1, or a fragment thereof. In another embodiment, the at least one peptide fragment of the α-synuclein protein comprises an amino acid sequence consisting of SEQ ID NO:2, or a fragment thereof. In another embodiment, the at least one peptide fragment of the α-synuclein protein comprises an amino acid sequence consisting of SEQ ID NO:3, or a fragment thereof.

In some embodiments the dendritic cell is autologous and may be obtained from the subject by leukapheresis. In some embodiments, the subject is a human subject. In another aspect, the present invention provides methods of treating symptoms of PD in a subject and/or passively vaccinating the subject against PD. The methods comprise administering an anti-α-synuclein peptide antibody to a subject in need thereof.

In another aspect, the present invention provides methods of inhibition of neurodegeneration, such as PD-induced neurodegeneration, in a subject and/or vaccinating the subject against PD-induced neurodegeneration. The methods comprise administering an anti-α-synuclein peptide antibody to a subject in need thereof.

In yet another aspect, the present invention provides methods of protecting against dopaminergic neuron cell death and/or NeuN positive cell loss in a subject. Dopaminergic neuron cell death and NeuN positive cell loss are known pathologies of PD. The methods comprise administering an anti-α-synuclein peptide antibody to a subject in need thereof, whereby dopaminergic neurons and/or NeuN positive cells are protected from cell death caused by α-synuclein mediated neurodegeneration. In another aspect, the present invention provides methods of reducing microglial activation in a subject. Microglial activation is another known pathology of PD. The methods comprise administering an anti-α-synuclein peptide antibody to a subject in need thereof, whereby microglial activation is reduced. In preferred embodiments, the anti-α-synuclein peptide antibody is specific for the N-terminal region of the α-synuclein protein. In some embodiments, the anti-α-synuclein peptide antibody is specific for a peptide with the peptide sequence of SEQ ID NO: 1. In other embodiments, the anti-α-synuclein peptide antibody is specific for a peptide with the peptide sequence of SEQ ID NO: 2. In other embodiments, the anti-α-synuclein peptide antibody is specific for a peptide with the peptide sequence of SEQ ID NO: 3.

In another aspect, the present invention provides a method of diagnosing PD in a subject, the method comprising:
determining a level of α-synuclein protein expression in a sample from a subject utilizing one or more anti-α-synuclein antibody that is specific for an amino acid sequence selected from SEQ ID NO:1, SEQ ID NO:2, and SEQ ID NO:3;
comparing the level of the α-synuclein protein expression in the sample to a reference expression value, wherein an elevated level of α-synuclein protein expression in the sample compared to the reference value indicates that the subject has PD. The reference expression value is obtained from a subject that does not have PD. In some embodiments, the sample is obtained from brain tissue.

EXAMPLES

The methods and compositions herein described are further illustrated in the following examples, which are provided by way of illustration and are not intended to be limiting. It will be appreciated that variations in proportions and alternatives in elements of the components shown will be apparent to those skilled in the art and are within the scope of embodiments of the present invention. Furthermore, many variations of the invention will become apparent to those skilled in the art upon review of the specification. Theoretical aspects are presented with the understanding that Applicants do not seek to be bound by the theory presented. All parts or amounts, unless otherwise specified, are by weight.

The following material and methods were used for all the methods and compositions exemplified herein.

Animals: Human α-Syn transgenic mice were purchased from Jax Laboratory (B6; C3-Tg(Prnp-SNCA*A53T) 83Vle/J, Bar Harbor, Maine stock number 004479) and were bred at the University of South Florida (USF) animal facility. Mice homozygous for the transgenic insert are viable and normal in size. These transgenic mice express human A53T variant α-Syn (full-length, 140 amino acid isoform) under the direction of the mouse prion protein promoter. At eight months of age, some homozygous mice develop a progressively severe motor phenotype. Presentation of the phenotype may manifest at 14-15 months of age (on average). The USF IACUC reviewed and approved the animal component of this research project, which was conducted in accordance with the United States Public Health Service's Policy on Humane Care and Use of Laboratory Animals.

Manifestations of minimal grooming, weight loss and diminished mobility precede movement impairment, partial limb paralysis, trembling and inability to stand. Immunohistochemistry analysis of mutants between 8 to 12 months of age indicates widely distributed α-Syn inclusions, with dense accumulation in the spinal cord, brainstem, cerebellum and thalamus. The appearance of α-Syn aggregate inclusions parallels the onset of the motor impairment phenotype. As well, axons and myelin sheaths exhibit progressive ultrastructural degeneration. Immunoelectron microscopy and biochemical analysis of this α-Syn expressing Tg strain demonstrate that the inclusions in neurons are comprised primarily of 10-16 nm fibrils of α-Syn. The structure, location and onset of the inclusions observed in the mutant mice resemble characteristics noted in human neuronal α-synucleinopathies, such as familial PD.

Figure 6:
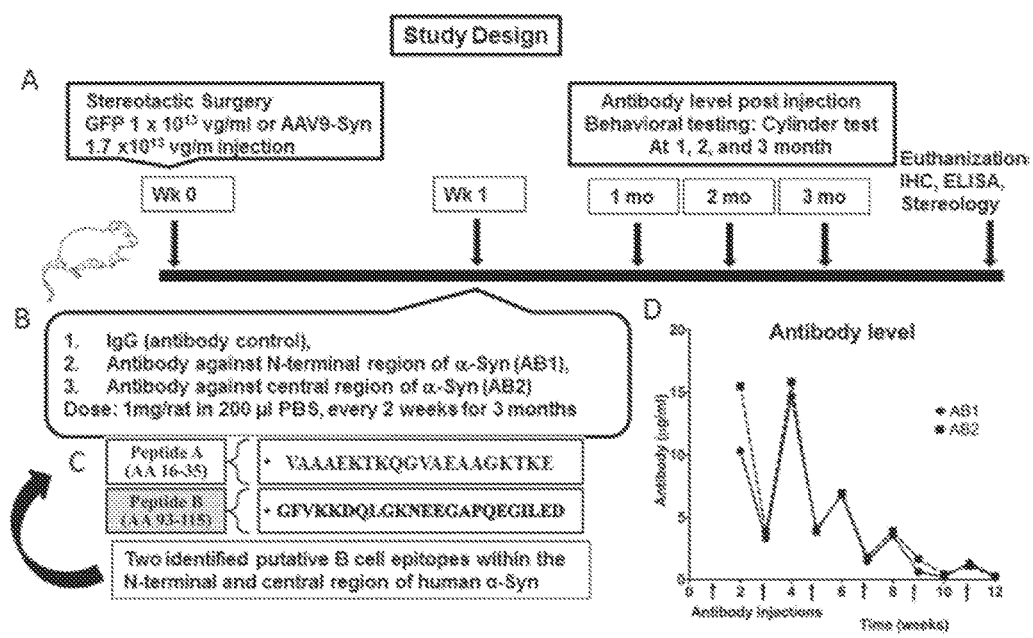
FIG. 6 shows the study design to test the efficacy of the anti-α-Syn antibody in a rat AAV-α-Syn PD model. A schematic diagram depicting (A) the details on AAV9 concentrations used and the time frame for AAV-9 injections and the behavioral testing, (B) the timing of the first antibody injections and initial dose, as indicated in the methods section the dose of the AB injected was reduced over time (C) the sequence of the antibodies and (D) level of serum antibodies taken 1 week after injections and just before subsequent injections. This demonstrates that antibody levels remained high for the first month and then clearance increased after 6 weeks. Times of injections are indicated by the arrows on the bottom of the graph.

Fisher 344 male rats (Harlan) were pair-housed in a 12 hour light/dark cycle with access to water and food ad libitum. Rats were randomly assigned to either 1) AAV-α-Syn+IgG (non-immune antibody control); 2) AAV-α-Syn-AB1 (treatment 1); 3) AAV-α-Syn-AB2 (treatment 2); or 4) AAV-GFP (negative control) groups (FIG. 6).

Recombinant human α-synuclein (rh-α-Syn) was prepared by Panoab Inc. (Tampa, Fla.) and α-Syn peptides used in this study were synthesized at the USF peptide center (Tampa Fla.) and Biomer Technology (Pleasanton, Calif.); all antibodies for western blotting and ELISA assay were provided by Panoab Inc. (Tampa Fla.); GM-CSF and IL4 were purchased from R&D (Minneapolis, Minn.). Cytokine kits were purchased from Millipore (Billerica, Mass.).

Peptide selection: Whole human α-synuclein protein was analyzed with DNAStar 8.1 software, and three major incontiguous B cell domains were predicted. The following three peptides were used in the present invention: (1) VAAAEKTKQGVAEAAGKTKE (SEQ ID NO: 1); (2) GFVKKDQLGKNEEGAPQEGILED (SEQ ID NO: 2); and (3) MPVDPDNEAYEMPSEEGYQDY (SEQ ID NO: 3) (FIG. 1A).

Dendritic Cell (DC) vaccine preparation and application: DCs were obtained and purified from bone marrow of 10 week old non-Tg littermates of the α-Syn Tg mouse breeding colony. Bone marrow isolation followed an established protocol, published in both Cao et al. and Luo et al. In brief, bone marrow was removed from 10 week old female C57BL/6 mice and the femurs cleanly excised, and all excess tissues were removed. Shortly thereafter, the bones were merged in cold phosphate-buffered saline (PBS), washed with ethanol, and again soaked in 1×PBS. After the ends of each femur were cut, bone marrow was flushed with medium (99% RPMI and 1% Antibiotics). Bone marrow was then gently re-suspended and passed through 70 μM sieves into a centrifuge tube. The mixture was centrifuged for 10 minutes at 1100 rpm, followed by removal of the supernatant and then a brief vortexing of the pellet. 5 mL ACK (0.15 M $NH_4Cl$, 1 mM $KHCO_3$, 0.1 mM EDTA, pH 7.3, at room temperature) was used for red blood cell lysis with an incubation period of 30 seconds while shaking; lysis was stopped by the addition of 45 mL HBSS. After centrifugation at 1,100 rpm (10° C. for 10 minutes), cells were suspended at $1×10^6$ cells/mL in medium (RPMI+10% FBS and 1% Antibiotics). GM-CSF and IL-4 (BD-Pharmgen, San Jose Calif.) were added to the media at the final concentration of 10 ng/mL, and cells were cultured in 6-well plates (3 mL/well). On the second day of DCs culturing, the medium was completely aspirated to remove all non-adherent cells (lymphocytes, progenitors, etc.), and 3 mL of fresh DC culture medium was added. The cells were allowed to grow in a $CO_2$ incubator (5% $CO_2$) and on day 4 were treated as follows: 1 mL/well old medium was aspirated and replaced by 1 mL/well fresh DC culture medium containing 60 μg/mL peptide (diluted to a final concentration 20 μg/mL). On the $8^{th}$ day, DCs were harvested and the supernatant collected for analysis (Luo et al., 2012) (Cao et al., 2008). The vaccine was prepared by sensitizing the antigen-presenting DCs with rh-α-Syn or α-Syn mixed peptides at 20 μg/mL for 7 days. After DCs were cultured, they were washed with 1×PBS twice and the concentration adjusted to $5.0×10^6$ cells/mL, followed by centrifugation, and then 200 μl of $1.0×10^6$ cells/mL were injected intravenously (i.v.).

Tg α-Syn mice cohorts. There were 4 groups used in the study. The Tg α-Syn expressing mice were grouped into the initial 2 treatment cohorts, the first being DCs sensitized with recombinant full length human α-Syn (designated Tg rh-α-Syn DC) and the second being DCs sensitized with the α-Syn peptides (designated Tg PSDC). The third group was a Tg mouse control group, which was vaccinated only with non-sensitized DCs (designated Tg DC control). A fourth and final group consisted of non-Tg littermate mice, which were used as a non-Tg, non-treated control (designated WT control). Each group of mice consisted of an n of 7. The treatment/vaccination schedule and schema is illustrated in FIG. 1A. Specifically, vaccinations were initiated in 3.5-month-old Tg mice, which functioned as the primary immunization (i.e. also designated as week 0). The subsequent initial 3 booster vaccinations/treatments were performed at 2-week intervals i.e., at 4, 4.5 and 5 months of age, corresponding to 2, 4 and 6 weeks following the initial vaccination. Two additional boosters were performed at 7.5 and 12 months of age, which were 16 and 34 weeks after the primary vaccination, respectively.

Blood Sample collection: Blood samples were collected, at time points indicated in the results section and figure legends, via the submandibular vein into an EDTA-containing tube after each vaccination. Plasma was separated by centrifugation at 9300 rcf for 2 minutes, and then aliquoted into screw-capped tubes for long-term storage at −80 C. All mice were euthanized after the last test of locomotor activity followed by collection of plasma and brain tissue for subsequent analyses.

DCs purity detection: CD11b antibody staining was used in this assay to identify the purity of DCs. Briefly, harvested DCs were incubated with anti-mouse CD11b-FITC (ebioscience, CA) for 15 minutes and washed with 1×PBS three times. Cells were then loaded onto a Flowcytometer (C6, Invitrogen).

Motor Behavior: Measurement of locomotor behavioral activity in vaccinated and control a-Syn expressing Tg mice: Coordinated locomotor activity was measured on a 47600-Mouse Rota-Rod rotometer purchased from Ugo Basile (Comerio VA, Italy). Briefly for this test, mice were placed on a rotating rod, which gradually accelerated from a rate of 4 to-40 rpms over a period of 5 minutes until the mice could no longer remain on the rod. The duration of time (seconds), designated as latency, that the mice remained on the rod was recorded, and each mouse was tested 5 times each day for 3 d. Data was expressed as mean latency (seconds+/−SEM) for each group of animals. A decrease in latency times in α-Syn Tg mice compared to the non-Tg control animals is indicative of depletion of SN levels of dopamine, the loss of which is correlated with the development of symptoms of PD. (Guerra et al., 1997; Meredith et al., 2006) As such, in these experiments higher latency values in vaccinated α-Syn Tg mice, compared to non-vaccinated Tg animals would be indicative of a protective effect of DC vaccination against dopamine depletion. A one-way ANOVA was performed and followed by Fisher's LSD test for the difference between groups.

Sandwich ELISA for blood and brain α-Syn level detection: Sandwich ELISA kits were obtained from Panoab Inc (Tampa Fla., USA) and manufacturer protocol was followed. On pre-coated plates, 100 μL diluted samples (diluted at 1:400 in blocking buffer) were added and incubated for 1 hour at 37° C. Second antibody (Anti-mouse IgG-HRP at 1:10000) was added after washing with washing buffer for 6 times and incubated at room temperature for 1 hour. After wash, TMB substrate was added for colorimetric detection and then stopped with 0.2 N $H_2SO_4$. OD values were recorded with a microplate reader. Concentration was calculated with a standard curve upon OD value.

Antibody Responses: Humoral immune responses against the α-Syn peptides were measured using the method reported by (Cao et al., 2008) with some modification. Briefly, the synthetic α-Syn peptide was immobilized at a concentration of 5 μg/mL (50 μl/well) in 96 well Immulon 4 plates (Dynatech Inc.) and incubated overnight at 4° C. Plates were then washed with washing buffer (0.45% NaCl in distilled/deionized water containing 0.05% Tween-20). After incubation, plates were washed again and subsequently incubated with the various dilutions of sera from vaccinated mice. After an hour, incubation plates were again washed and incubated with 100 μl of a goat anti-mouse IgG-HRP conjugate diluted in blocking buffer for 1 hour at 37° C. Following this, incubation plates were again washed with a 1 mg/ml solution of TMB substrate. After color development, the reaction was stopped by addition of 25 μL of 2N $H_2SO_4$ per well. Plates were then read on an ELISA plate reader/spectrophotometer at 450 nm. OD values were then graphed versus dilution of sera.

Western blotting for α-Syn: Lysate of mice brain tissue was quantified and prepared with Tris-Glycine SDS PAGE electrophoresis with reducing reagents. All antibodies against α-Syn were obtained from Panoab Inc. (Tampa, Fla. 33612).

Brian Tissue Preparation: All mice were deeply anesthetized followed by intracardiac perfusion with PBS solution. Hemi-sectioned brain was put into 4% paraformaldehyde for pathological analysis, and the other half of brain was rapidly frozen with dry ice for chemical analysis. Brain tissue was lysed with RIPA buffer containing protease inhibitors. Total protein was quantified, adjusted and loaded on a Tris-Tricine 12% gel and separated for 4 hours under 60V. Transfer was performed at 36V overnight on to PVDF membrane and then applied with α-Syn polyclonal antibody (provided by PanoAb Inc. Tampa Fla. USA). 1:5000 anti-goat IgG-HRP was used as secondary antibody.

Cytokine Level Determination: Milliplex MAP Kits for mouse Cytokine/Chemokine were used from Millipore Corp. (Billerica, Mass.).

Vector Construction and AAV-α-Syn Administration through Stereotaxic Surgery: A recombinant adeno-associated viral vector (rAAV) serotype (Games et al., 2014) expressing human wild type (WT) α-Syn or green fluorescent protein (GFP) under control of the CBA promoter was produced and purified according to the methods described by Carty et al. (2010). The human α-syn clone was confirmed to be reference number GI:225690599. A dot blot assay was used to determine the viral titer and was expressed as vector genomes (vg)/ml (Carty et al., 2010). Animals were injected with 1.5 µL of human α-Syn AAV9 (~1×1013 vg/mL) or control GFP virus (~1×1013 vg/mL) into the right SN at a flow rate of 2.5 uL/min. The virus was injected using the CED method described previously (Carty et al., 2010). Surgery was performed as described previously (Gorbatyuk et al., 2010). Injection coordinates for delivery of the recombinant AAV were the following: anteroposterior: −5.6 mm, lateral: −2.4 mm from bregma, and dorsoventral: −7.2 mm from dura.

Generation of anti-α-Syn antibodies and intra-peritoneal delivery: Two major B cell epitopes within the full length human α-Syn protein were identified based upon antigenicity analysis using DNASTAR Lasergene software (FIG. 6). Peptides spanning these two major B cell epitopes were synthesized by Biomer Technology (CA, USA). The peptides were designated fragments A and B which span the N terminal and central regions of the protein respectively (sequence shown in FIG. 6C). Each of the peptides (250 µg each) were used to vaccinate six month old female boyer goats in order to generate peptide specific antibodies. A series of 3 injections at 3 week intervals were performed. The first injection was with 500 µg peptide mixed with MPL adjuvant. The two subsequent injections were 250 µg peptide mixed with MPL adjuvant. The inoculated goats were bled two weeks after each inoculation to check the antibody response by standard ELISA methods as described below.

Anti-peptide antibodies were purified by mixing the goat antisera with peptide conjugated magnetic beads (Pierce Biotechnology, Rockford, Ill.). Beads were generated as per the protocol provided by Pierce Biotechnology. Briefly, the peptide conjugated magnetic beads were incubated with the goat antisera. Beads were concentrated using a magnet and the beads were washed followed by elution of purified antibody from the beads by standard methods (Anderson et al. 2009). Control non-immune goat IgG was purified for use in the experiments using protein G (PanoAb Inc., Temple Terrace, Fla.). In the study reported here only antibodies against the AB1 (N terminal) and AB2 (central region) of the protein were used as our primary interest was to examine regions outside of the C-terminus. In future studies we will compare results with the C terminal that has been reported by others (Bae et al., Ghochikyan et al., 2014).

Antibodies, either control IgG, AB1 or AB2 were injected intraperitoneally (i.p.) at 1 mg/rat in 200 µl PBS for the first two injections, then reduced to 0.5 mg/ml for the subsequent 2 injections, and reduced to 0.25 mg/ml for the final injections. Antibody injections were performed one week after intracranial injection of the AAV9-α-Syn with subsequent administrations every 2 weeks for 3 months. Blood from the treated and control rats was periodically sampled (just prior to injection and one week after each injection) in order to measure, by ELISA, sera antibody levels. These time points for administrations samplings, and analyses are indicated in FIG. 6. Antibody levels increased after injections, however, the clearance of antibody increased over time.

Determination of potential antibody treatment effects on behavioral deficits in α-Syn expressing rats as measured by the paw use bias cylinder test: At one, two and three months following stereotaxic surgical delivery of the AAV9-α-Syn vector or controls, measurement of potential effects of antibody administrations were made using the cylinder test which assesses paw use bias. This test is a straight-forward and valid analysis of unilateral defects in voluntary forelimb use which was originally utilized for the detection of limb impairment in rats with unilateral 6-hydroxydopmaine lesions, another model for PD (Cenci, 2005). Subsequent use of the cylinder test in other rat and mouse models of PD has further confirmed this to be a simple and efficient method for measuring lesions, which affect forelimb use (Schallert et al., 2000; Iancu et al., 2005; Kirik et al., 2002). Moreover, this test is designed to score animal paw movements initiated by the animal without influence from the experimenter. As well, this test measures the asymmetry between the affected and unaffected limbs with each animal functioning as its own control for individual differences in forelimb impairments. Briefly, for this test rats were placed in a 4-liter transparent upright Plexiglas cylinder measuring 30 cm high by 20 cm in diameter. The number of either left or right or both forelimb placements on the wall of the cylinder were recorded, and the percentage of each limb or both limbs placements compared to the total limb placements was calculated. At least twenty paw touches per rat were recorded for the analysis.

Immunohistochemistry and Stereological Quantification: Following behavioral testing rats were divided into two groups with even distribution of paw bias scores. One group was used for biochemical analyses (described below), and the other group was used for immunohistochemistry (IHC). For IHC rats were anesthetized with isoflourane and perfused transcardially with phosphate buffered saline (PBS), followed by treatment with 4% paraformaldehyde in PBS. The brains were carefully removed and postfixed in paraformaldehyde overnight followed by equilibration in 30% sucrose in PBS for at least 24 hours. The brains were then sectioned into 40 µm coronal slices with every sixth section within the SN selected for immunostaining. Tyrosine hydroxylase (TH) activity was measured since this enzyme is the rate limiting step in the generation of dopamine, and is specific for the dopa-minergic neurons in the SNc. The diminution of dopamine has been demonstrated to be correlated to α-Syn levels (Alerte et al., 2008). For immunohistochemical analysis, brain slices were first incubated in sodium periodate (PBS/NaIO4) for 20 minutes, then blocked in PBS/0.1% Triton X-100/3% normal goat serum for 1 hr and incubated overnight with the appropriate primary antibodies (mouse anti TH, Immunostar, 1:10,000; OX-6-mouse anti-RT1B 1:750. BD, mouse Anti-NeuN, Millipore (1:100), purified goat polyclonal anti-α-Syn (1:30000 from 1 mg/ml stock). Slices were then washed and incubated for 1 hour in biotinylated secondary antibodies goat-anti mouse or rabbit-anti-goat followed by three washes before one hour incubation in an avidin-biotin substrate (ABC kit, Vector Laboratories). Slices were then incubated in DAB (diaminobenzidine) solution with metal enhancer for OX-6, NeuN, and Syn staining or without metal enhancer for TH staining. Slides were dried, dehydrated through a graded alcohol series into xylene and cover-slipped with permount mounting medium. The Optical Fractionator method of unbiased stereological cell counting was used to estimate the number of TH+, NeuN+, and OX-6+ cells in the SN. The sections were viewed on an Olympus BX-60 microscope (Melville, N.Y.) using a CCD video camera (HV-C20, Hitachi, San Jose, Calif.). Contours were determined at 2× magnification and cell counting was performed at 40× using the optical fractionator. The sampling site was customized to count at least 200 cells per brain. For counting TH, NeuN, and OX-6 positive cells, the counting frame were 70×70 μm 75×75 μm and 400×300 μm with a virtual counting grid of 140×140 μm, 160×160 μm, and 400×300 μm, respectively. For quantification of α-Syn immunoreactivity, every 6th brain section throughout the region of interest were imaged using a Mirax Scan digital slide scanner (Carl Zeiss USA). The percent area of positive α-Syn staining in the SN slides was quantified using Image analysis software (NearCYTE) as described previously (Carty et al., 2010).

Measurement of brain human α-Syn levels and levels of administered anti-peptide antibodies: For biochemical analysis, a separate group of rats (AAV-GFP control [n=5], AAV α-Syn+IgG [n=6], AB1 [n=5], and AB2 [n=5] were perfused with PBS and brains were snap-frozen in liquid nitrogen and stored at −80° C. until assayed. α-Syn level detection: A sandwich ELISA kit (Biomer Tech, Inc) was used to determine α-Syn levels in brain tissues. Briefly, a series of 50 μL of α-Syn protein as standards (1250, 625, 313, 156, 78, 39, 19.5 and 0 pg/ml) were added to a 96 well plate pre-coated with goat anti-human α-Syn antibody (250 ng/well). This constituted the standard curve for the analysis. The other wells of the plate had added to them brain lysates (250 μg of protein) samples from the different experimental and control groups. Then 50 μl of rabbit-anti-human alpha synuclein antibody (i.e. detection antibody which had antigen specificity against α-Syn distinct from that of the capture antibody was added into each well and mixed on an orbital shaker. The plate was then incubated for 3 hours at RT. Following the incubation the plates were washed and subsequently incubated at RT with Biomer Tech anti-rabbit AP (alkaline phosphtase) conjugated antibody (1:5000 dilution, 100 μl/well). This was followed by another washing and incubation with diluted BioFXUltra Sensitive AP 450 nm solution for 20 min 100 μl/well at a 1:10 dilution. The plate was then subsequently read at 450 nm (for chemiluminescense) with concentration levels calculated based on the standard curve. Detection of injected antibody. Plates were coated with the α-Syn peptides (500 ng of individual peptides per well) used to generate the antibodies and incubated overnight at 4° C. After blocking for 1 hr in 1.5% BSA-PBST, 100 μL/well of the rat plasma samples at a 1:200 dilution in 1.5% BSA-PBST were added and incubated overnight. Normal goat IgG used as a standard in this assay. Following another wash, 100 μL/well of anti-goat IgG-HRP (horseradish peroxidase) (A-9452) in 1.5% BSA-PBST was added and incubated at 37° C. for 45 min. The plate was then incubated with BioFX substrate (100 μL/well) for 5 min at RT after several washes and then measured at 450 nm for chemiluminescence.

Data analysis: One-way analysis of variance (ANOVA) was used for multiple group analysis, with the significance level α=0.05, as indicated, for every set of experimental data with the exception of the cylinder test where a two-way repeated measures ANOVA was used. A Bonferroni's post hoc test was conducted to assess further differences among groups. All values were expressed as mean±SEM. Graphs were generated, and statistical analyses performed using GraphPad Prism 5.0 (GraphPad Software, La Jolla, Calif., USA). α-synuclein and cytokine results were analyzed with one-way ANOVA and followed by post-hoc Turkey test between groups.

Example 1—Vaccines with Sensitized DCs

Antigenicity analysis of h-α-Syn protein revealed several major B cell epitopes, and no T cell epitopes. The three major B cell epitopes were selected as the peptides for sensitization of DCs. FIG. 1A indicates the schedule for a-Syn peptide/a-Syn recombinant protein or control sensitized DC vaccinations as well as the time points when locomotor (i.e., rotometry) and immune analysis was performed. FIG. 1B indicates the location (amino acid numbers) and sequence of the 3 identified B cell epitopes within α-Syn from which the 3 DC sensitizing peptides were generated.

Figure 2:
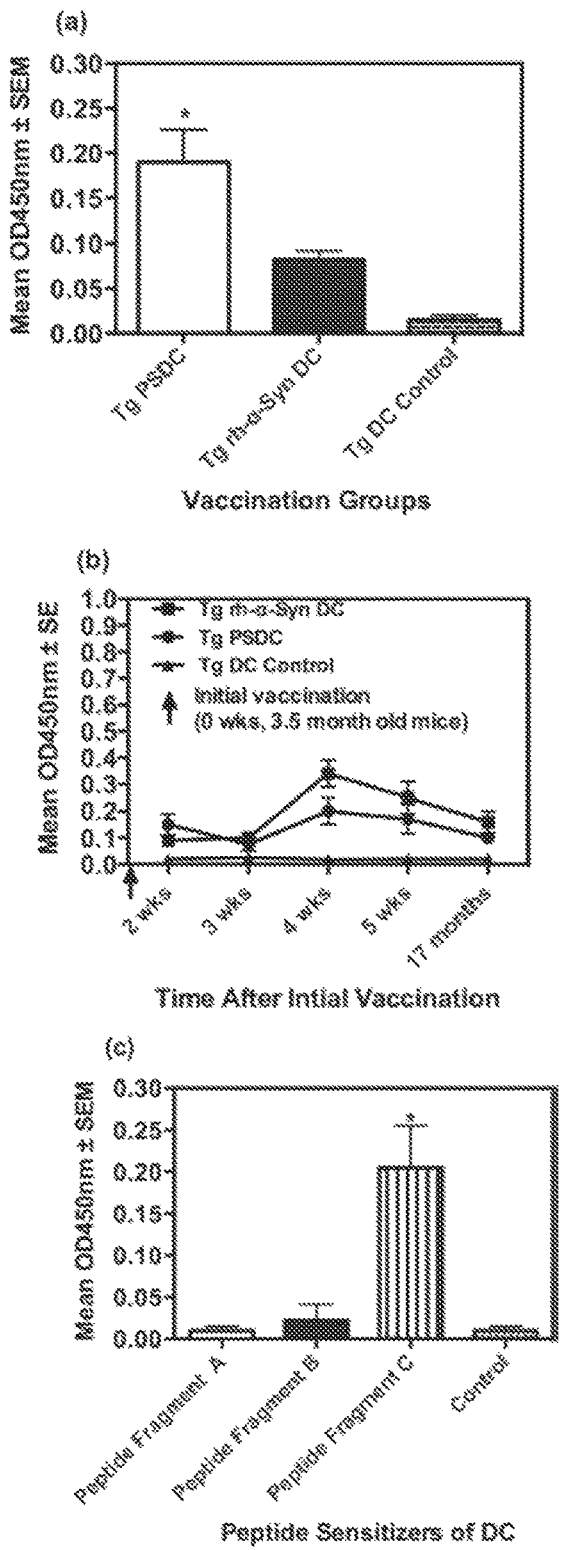
FIG. 2 shows anti-α-Syn antibody responses elicited by peptide-sensitized DC (PSDC) or rh-α-Syn or rh-sensitized DC vaccines as measured by ELISA. (A) Ten days following the initial vaccination PSDC administered Tg (i.e. Tg PSDC) mice demonstrated a significantly higher anti-α-Syn antibody response, measured by OD450 nm values, than did Tg mice vaccinated with rh-α-Syn sensitized DCs (i.e., Tg rh-α-Syn). OD450 nm binding values are also provided for non-sensitized PSDC vaccinated mice (i.e. Tg DC Control). (B) Time course of anti-α-Syn antibody responses from analysis of sera from either PSDC (i.e., Tg PSDC) or rh-α-Syn DC sensitized (i.e. Tg rh-α-Syn DC) vaccinated mice. OD450 nm binding values are also provided for non-sensitized DC vaccinated mice (i.e., Tg DC Control) (C) Demonstration that sensitization of DCs with peptide fragment C resulted in the highest anti-α-Syn peptide antibody responses of the 3 peptides tested. For analysis of data presented in (A), (B) and (C) above statistical significance was determined by the student t test with differences being significant at the 0.05 level and are indicated by *.

PSDC, administered by intravenous (i.v.) injection into Tg a-Syn mice (Tg-PSDC), induced a more vigorous ($p<0.05$) antibody response measured by ELISA against rh-a-Syn (i.e. 0.20+/−0.04 OD450 nm units) after one immunization (quantitated 10 d post-immunization) than the did rh-α-Syn-sensitized DCs (Tg-rh-α-Syn DC) vaccinated group (i.e., 0.08+/−0.01 OD450 nm units). Background antibody binding levels in sera from non-sensitized DC vaccinated mice were at 0.015+/−0.005 OD450 nm units. These data are presented in FIG. 2A. However, antibody levels against rh-α-Syn in mice vaccinated with rh-α-Syn sensitized DCs increased after the 3rd vaccination and remained slightly higher or comparable for the duration of the study compared to the antibodies generated in the Tg-PSDC group (FIG. 2B). The results indicate that the DC vaccine sensitized with the pooled peptides induced levels of anti-α-Syn specific antibodies more rapidly than the DC vaccine sensitized with rh-α-Syn, even though with time the levels of antibodies in the 2 groups became comparable. Epitope mapping of the anti-sera generated from the vaccinated animals revealed that antibodies produced by PSDC DC vaccination exhibited significant ($p<0.05$) binding (0.21+/−0.05 OD450 nm units) only to α-Syn peptide fragment C. Binding to α-Syn peptide fragments A and B was 0.01+/−0.005 and 0.02+/−0.002 OD450 nm units respectively (FIG. 2C). Negative control binding was at 0.012+/−0.005 OD450 nm units. Therefore, binding of antisera to peptides A and B was at background levels. These data suggest that peptide fragment C contained the major B cell epitope which mediated effective DC sensitization.

Example 2—Locomotor Performance in Mice Treated with Sensitized DCs

Figure 3:
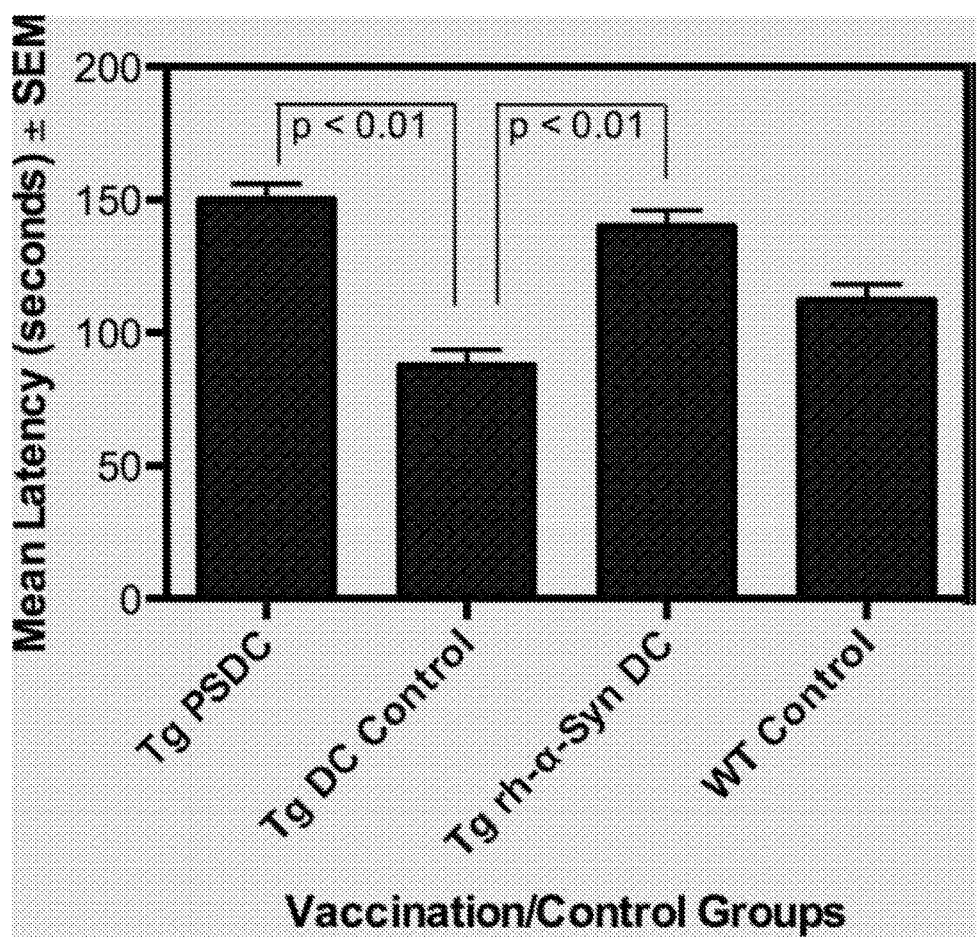
FIG. 3 shows a graph of the rotometric locomotor performance of Tg mice at age 17 months after the vaccination regimen with either PSDC or rh-α-Syn sensitized DCs. The PSDC (i.e. Tg PSDC) or rh-α-Syn sensitized (i.e., Tg rh-α-Syn) DC vaccinated Tg mouse groups performed significantly better (i.e. higher latency values) on the rotorod test than did Tg mice vaccinated with non-sensitized DCs (i.e., Tg DC Control). Latency values are also provided for WT (wild type) control mice (i.e. WT Control).

There was no difference in locomotor performance on the rotorod between the 4 groups of mice after 5 vaccinations that is, at 9.5 months of age (data not shown). However testing of the mice shortly before euthanasia (at 17 months), after they had received a total 6 immunizations revealed that Tg-PSDC and Tg-rh-α-Syn vaccinated mice exhibited ($p<0.05$), locomotor performance (i.e., lateney times) scores (150+/−6 and 140+/−6 seconds respectively), compared to the Tg DC control or wild type (WT) control groups scores (87+/−6 and 112+/−6 seconds respectively). These data are presented in FIG. 3. There was no difference in the mean lateney time scores between the Tg-PSDC and Tg-rh-a-Syn vaccinated mice, suggesting that both α-Syn peptide and α-Syn recombinant protein sensitization of DCs for use as a cell based vaccine/therapy, were comparably effective in ameliorating some of the locomotor behavioral defects characteristic of the a-Syn expressing Tg mice.

Example 3—α-Syn Levels in Mice Treated with Sensitized DCs

Figure 4A:
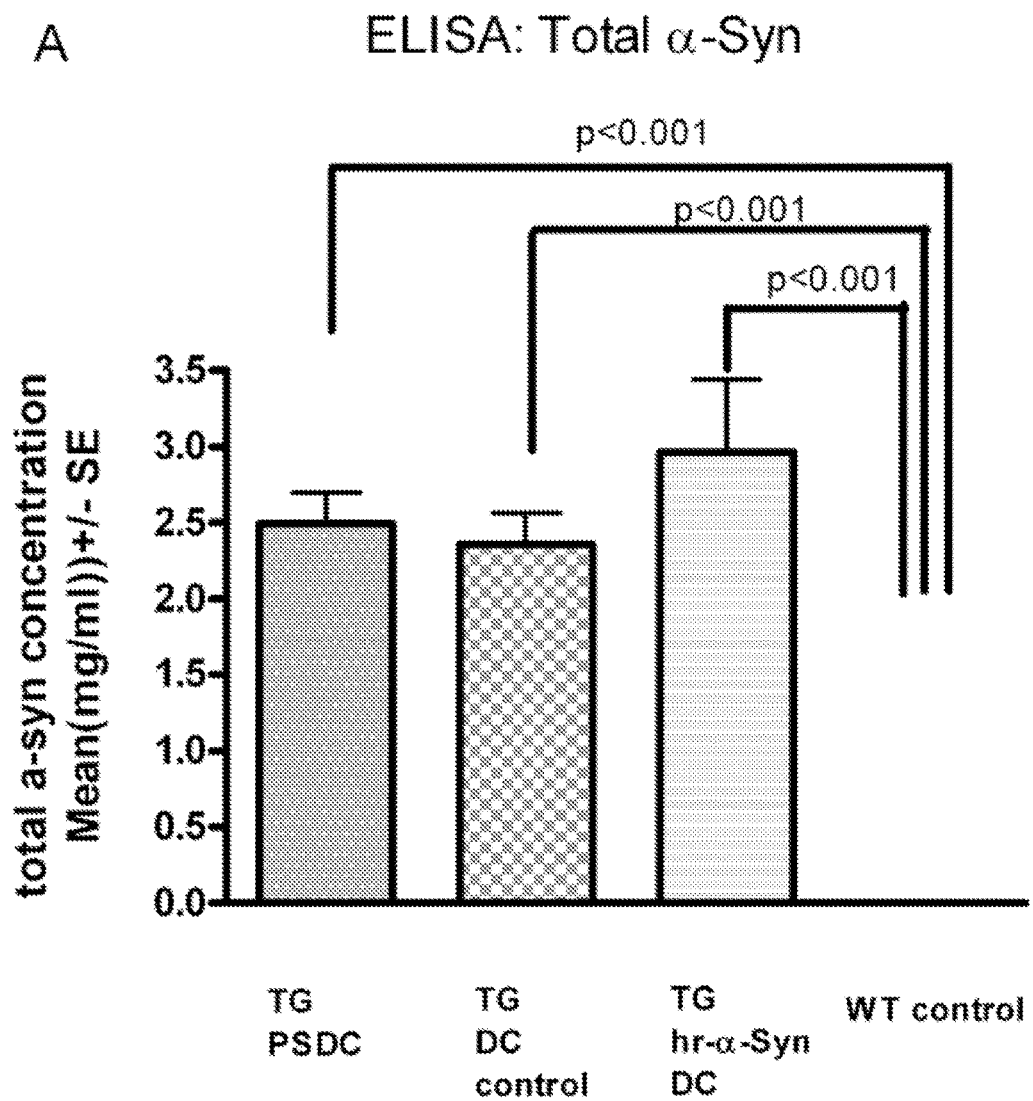
FIG. 4 shows rh-α-Syn levels in (A) plasma as measured by sandwich ELISA assay (n=7) and (B) brain tissue lysates as measured by Western blot. Western blotting was conducted with antibody generated from goat against pooled peptides to all brain tissues. Anti-Mouse β-actin was used as housekeeping protein detection to make sure the protein level is more comparable among samples.
Figure 4B:
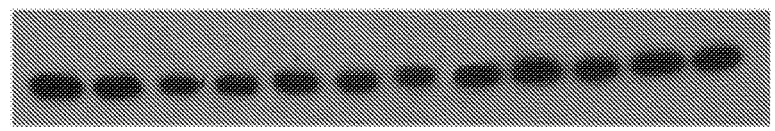
Figure 4B:
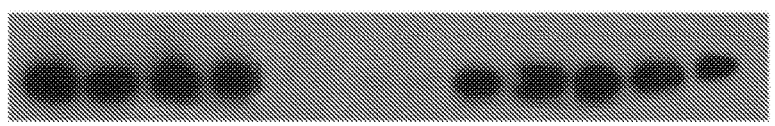
Figure 4B:
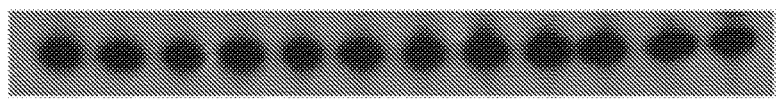
Figure 4B:
Figure 4C:
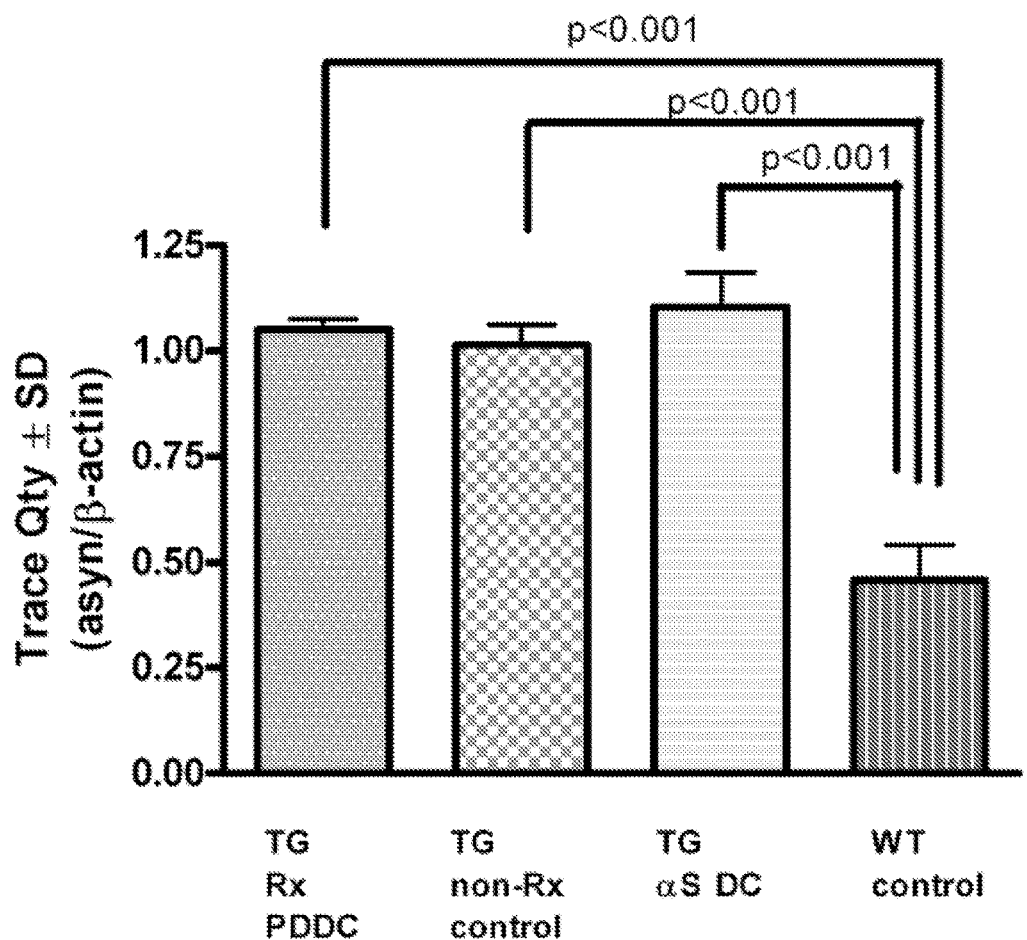

Plasma levels of α-Syn protein were significantly decreased after the second vaccination in the PSDC group, but not in the rh-α-Syn-sensitized DC group. However, levels of plasma α-Syn protein returned to levels seen in control Tg mice just prior to euthanasia at 17 months (FIG. 4A). Brain monomeric α-Syn levels in mice treated with PSDC or rh-α-Syn-sensitized DCs were not significantly different (FIGS. 4B and 4C).

Example 4—Cytokine Profiles of Mice Treated with Sensitized DCs

Figure 5A:
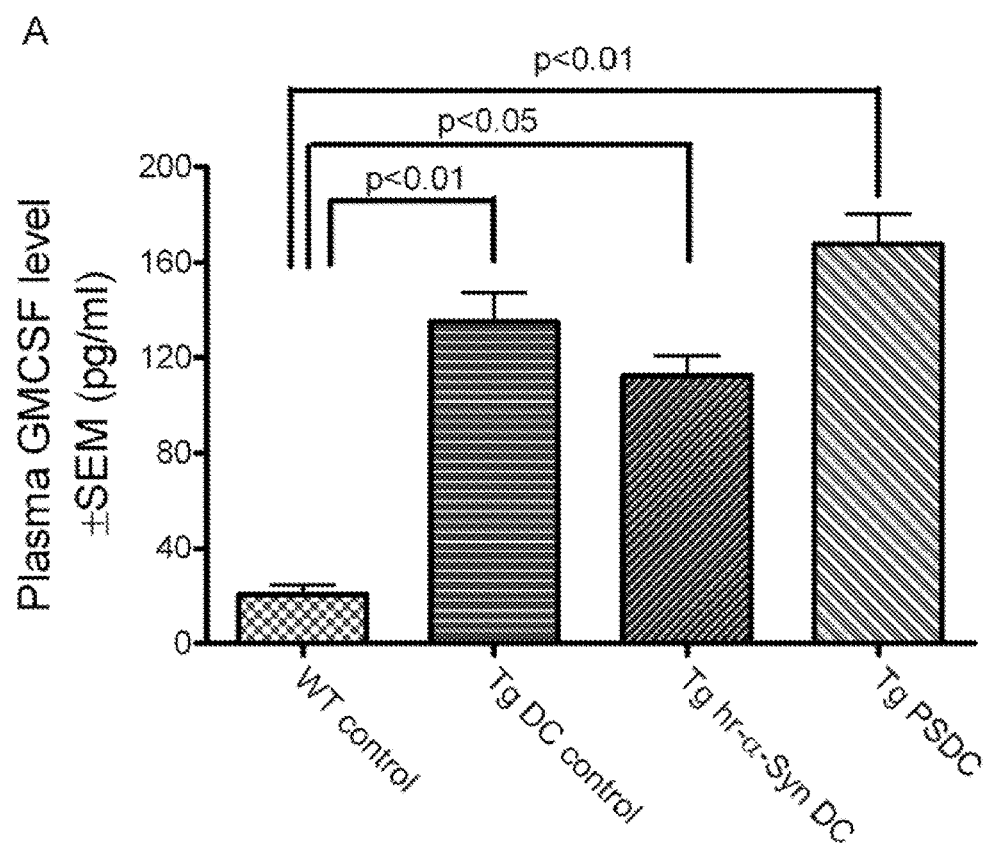
FIG. 5 shows (A) GM-CSF levels in brain tissue measured by Luminex assay for mice treated with Tg PSDC, Tg rh-α-Syn DC, Tg DC control, and WT control; and (B) IL-1α levels in brain tissue measured by Luminex assay for mice treated with Tg PSDC, Tg rh-α-Syn DC, Tg DC control, and WT control. (C) Levels of the pro-inflammatory cytokine IL-1α in brain lysates from PSDC or rh-α-Syn sensitized DC vaccinated mice. Levels of IL-1α in brain lysates are expressed as pg/ml+/− SEM. The results indicate that significantly lower levels of IL-1α were measured in the brain lysates from PSDC or rh-α-Syn sensitized DC vaccinated Tg mice than in non-sensitized DC vaccinated Tg controls. IL-1α levels are also provided for WT (wild type) control mice (i.e., WT Control).
Figure 5B:
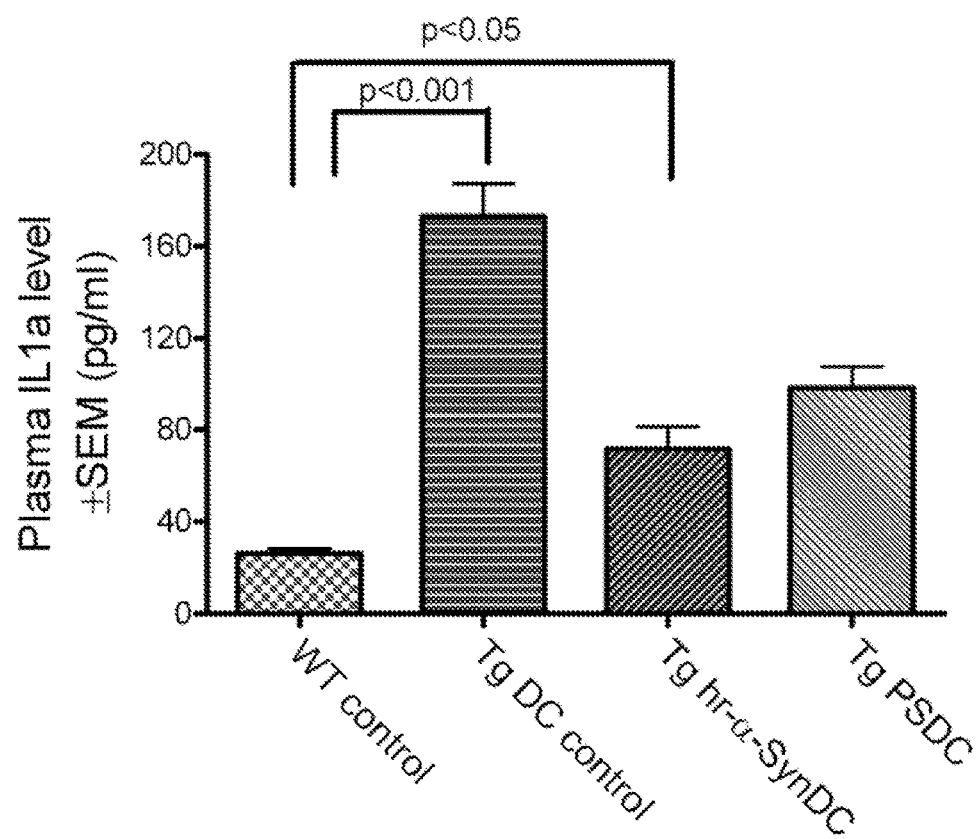

Assays of the cytokine profile did not reveal evidence for a generalized inflammatory response, but instead there was a decrease in IL-1α, a pro-inflammatory cytokine (FIG. 5B). Treatment with antigen-sensitized DCs resulted in significant lowering of IL1α, a known pro-inflammatory cytokine (n=7, P<0.05). Also, peptide sensitized DCs vaccine boosted GM-CSF, a major neurogrowth factor, production (FIG. 5A). Mice treated with PSDCs showed the highest GM-CSF level in brain than all other groups. (P<0.05, n=7) This Tg mouse model of α-synucleinopathy showed absence of cell death; therefore, it is not possible to ascertain here whether this treatment approach would be effective in preventing DA neuronal death as occurs in PD.

Figure 5C:
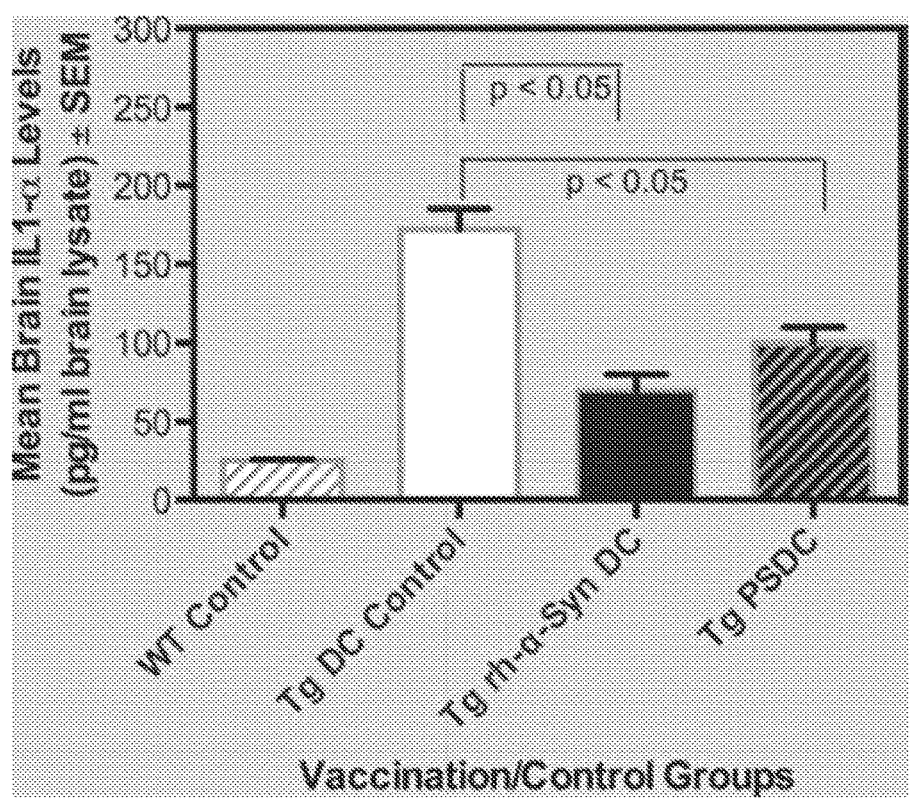

Upon euthanization of mice at the 17 month time point, brains of mice from the different vaccinated and control groups were prepared for measurement of the pro-inflammatory cytokine IL-1α: The IL-1 family of cytokines have a significant role in neuroinflammation, with levels of IL-1α and β as well as other pro-inflammatory cytokines being elevated in the brains of AD and PD patients. (Shaftel et al., 2008; Hirsch et al., 2009; Basu et al., 2004) As such, IL-1α levels in brain lysates, prepared as indicated above, were measured in the non-Tg WT as well as experimental and control vaccinated αSyn expressing Tg mice. Data on levels of IL-1α are indicated in FIG. 5C and are expressed as mean pg/ml brain lysate+/−SEM. Specifically, mean IL-1α levels were 25+/−1, 172+/−13, 70+/−10 and 100+/−10 pg/ml brain lysate in WT control, Tg DC control, Tg rh-αSyn DC and Tg PSDC mouse groups, respectively. Importantly, it was determined that the levels of IL-1α in the brains of Tg rh-αSyn DC and Tg PSDC mice were significantly (p<0.05) decreased compared to the Tg DC control mice. These results suggest that the DC vaccines sensitized with either αSyn peptides or full-length αSyn protein mediated a decrease in the brain levels of IL-1α, a cytokine that, as indicated, is associated with neuroinflammation and is often elevated in the brains of PD patients.

In a further analysis of the data parameters generated in this study, Pearson correlation (r) determinations were performed, which assessed potential associations between sera anti-α-Syn antibody levels, brain IL-1α levels and locomotor rotometry latency values. Specifically, r-values comparing (a) antibody levels to IL-1α levels, (b) antibody levels to latency values and (c) latency values to IL-1α levels were −0.94, 0.99 and −0.91, respectively. Importantly, these analyses indicate a positive correlation between anti-α-Syn antibody levels and latency values, suggestive of a causal relationship between antigen specific antibody levels and protection against locomotor deficits Likewise, there was a negative correlation between levels of anti-α-Syn antibodies or latency values to IL-1α levels. Overall, the results of these determinations are further supportive evidence of the ability of the α-Syn peptide/protein sensitized DC vaccines to induce antigen specific immune responses which reduce (a) the inflammatory profile in these Tg mice as well as (b) the loco-motor deficits characteristic of the α-Syn expressing Tg mouse strain.

Discussion of Examples 1-4

The application of immune based interventions against Alzheimer disease (AD) has recently being applied to Parkinson disease (PD), the second most common neurodegenerative disorder. Several years ago, the first antigen-loaded DC vaccine against AD was developed and tested in a mouse model. (Cao et al., 2008). This cell-based approach to vaccination generated a long-lasting antibody response without eliciting significant inflammation. Specifically in the present invention, a similar cell based DC vaccine approach was applied to a PD mouse model Tg which targeted α-Syn. As such, the results presented here indicated that DCs sensitized with full length rh-α-Syn or peptide fragments from h-α-Syn, were effective in triggering the generation of anti-α-Syn antibodies in a Tg α-Syn expressing mouse model of PD synucleinopathy.

The α-Syn peptide fragments used in this invention as sensitizers of DCs were generated based on B cell epitope antigenicity analysis of full human α-Syn amino acid sequence. Specifically, 3 major B cell epitopes were identified followed by the synthesis of 3 peptide fragments, each containing one of these epitopes. These peptides were combined as a peptide/antigen mixture and used to stimulate mouse bone marrow-derived DCs. The full-length recombinant protein (rh-α-Syn) was also used to sensitize DCs, as a putative positive control. DCs sensitized with the peptide fragment pool (PSDC), when used as a cell based vaccine, elicited a temporally more rapid antigen specific antibody response than did DCs sensitized with full-length rh-α-Syn. This is hypothesized to be due to bypassing of the typical antigen processing steps which generate small peptides from protein antigens, which in turn bind to MHC molecules with subsequent binding of this complex to the TCR of T cells leading ultimately to activation.

Epitope mapping data using anti-sera generated from the DC vaccinated animals verified the antigenicity predicted by analysis with DNAStar 8.1 software, as described in the Materials and Methods. One of the epitopes evaluated (i.e. within peptide C) appears to be the critical antigen that elicits a functional antibody response. Therefore, the epitope displayed in peptide C is an important target for the development of immune based preventatives/therapies.

Rotometry locomotor behavioral testing demonstrated that both peptide and rh-α-Syn sensitized DC vaccinated Tg mice performed better, in terms of ability to remain on the rod longer (i.e., higher latency values), than the non-sensitized DC control vaccinated Tg mice. Despite the improvement in locomotor activity in the vaccinated mice, levels of soluble brain α-Syn measured after euthanasia were not different between the groups (data not shown). While it is possible that the assay fails to measure total (insoluble and soluble) α-Syn, a more likely explanation may relate to the mouse model used. Specifically, the PD model used in this study greatly overexpresses α-Syn, to levels considerably higher than those observed in physiological or pathophysiological circumstances. When used in a system that expresses more moderately elevated levels of α-Syn consistent with typical pathology, the cell based DC vaccine used in this study may, in fact, demonstrate a reduction in total α-Syn levels. Another possibility is that the animals were not provided sufficient vaccinations, especially after 12 months of age. In this invention, the last treatment was at 12 months of age, with euthanasia and post-mortem analyses being performed at 17 months of age.

As indicated, a range of immune-based interventions, including vaccination with the Ab peptide, (Morgan et al., 2000) and passive delivery of antibodies against Ab have all been demonstrated to be effective, to some extent, in APP/PS1 Tg mouse models of AD, in terms of decreasing Ab deposition and ameliorating memory deficits in this murine system. (McLaurin et al., 2002) However, transition of findings in these animal models to human clinical trials has resulted in the development of adverse effects including hemorrhages and encephalitis, which obviously need to be prevented if this vaccination is to have any clinical utility. As well, immune tolerance to Ab as well as immunization, in the context of an aging immune system, are likewise limitations of vaccine-based interventions. (Vasilevko et al., 2009; Cicin-Sain et al., 2010) Therefore, as indicated, in order for immune based therapies to be utilized, a number of different challenges need to be overcome. To compensate for age related diminution of immunity a potent immune stimulating adjuvant is often necessary to be included in the vaccine preparation. Unfortunately, such adjuvants often result in over-activation of the immune system with concomitant elicitation of a massive T cell response. These T cells may then infiltrate the brain through a leaky blood brain barrier culminating in neurologic adverse events including encephalitis. Specifically, as indicated above, this observation was made in a subset of subjects in an Ab vaccine clinical trial. (Sela et al., 2002) Interestingly however, a follow-up on individuals in this clinical trial revealed that those exhibiting anti-Ab antibodies had, to some degree, attenuation of clinical symptoms. (Sela et al., 2002) This finding suggests that irrespective of some of the adverse effects noted in the trial, an immune based strategies against neurodegenerative diseases such as AD are worth pursuing.

Using studies on AD as a precedent, vaccines and immunotherapies targeting the intracellular protein α-Syn have also been evaluated in animal models of PD. (Mougenot et al., 2010; Hirsch et al., 1985; Masliah et al., 2005) A traditional vaccination approach against PD will have similar challenges and safety concerns as noted with immune based strategies against AD. Among the challenges with targeting α-Syn in vaccine and immunotherapeutic strategies, as is the case with Ab for AD, is that α-Syn typically functions as a self-protein. Therefore, this protein will likely exhibit immune tolerance, particularly in the context of the α-Syn expressing Tg mouse model used in the study. However, several studies have indicated that antigen sensitized DCs, when used as a vaccine, can overcome (i.e., break) immune tolerance. This has been specifically reported in a mouse model of scrapie induced by prion proteins, (Bachy et al., 2010) as well as in mouse models of tumor induction (Okano et al., 2005) and hepatitis B infection. (Farag et al., 2012) Also, as previously indicated both α-Syn and Ab have successfully been able to stimulate antibody responses in appropriate Tg animal models. (Mougenot et al., 2010; Morgan et al., 2000) Therefore, the potential problem of immune tolerance to α-Syn can be overcome by various strategies including the use of antigen sensitized DC vaccines. Cell based DC vaccines may provide safer and more effective approach against neurodegenerative diseases such as AD and PD. Dendritic cell vaccines have been widely studied and are currently being applied for treatment of cancers. (Barrou et al., 2004; Cohen et al., 2005; Gajewski et al., 2001; Loveland et al., 2006; Mittendorf et al., 2006; Satthaporn et al., 2001) Most investigations have focused on the major ability of DC based vaccines to stimulate CD8C T cells. (Yu et al., 2004; Nair et al., 2000) However, there is evidence as well that DC based vaccines can stimulate antigen specific B cells with the concomitant release of antibody. (Yu et al., 2004; Nair et al., 2000; Gruber et al., 2007; Boscardin et al., 2006) As such, it is hypothesized that the protective biological activity of the DC vaccine used in this study and noted in the α-Syn expressing Tg mouse model is likely mediated by α-Syn specific antibodies. In fact, previous published data from our group indicate that DC vaccines are able to redirect the immune response toward a Th2 anti-inflammatory response which decreases the likelihood for the generation of adverse effects often noted associated with pro-inflammatory Th1 immune responses. (Nabar et al., 2012; Luo et al., 2012)

There are significant advantages with the use of dendritic cell vaccines including: (a) ability to serve as self-adjuvants with no additional stimulation of the immune system required and therefore likely decreasing the chances for developing adverse inflammatory responses and (b) the fact that DCs are collected autologously from patient effectively eliminating the chance of tissue/cell rejection.

Overall, this invention has identified the most effective peptide fragment of α-Syn with which to vaccinate mice to successfully produce protective anti α-Syn antibodies in the context of a cell-based DC vaccine. In addition, this invention demonstrated that the DC vaccination strategy reduced levels of the pro-inflammatory cytokine IL-1α, which suggests that the α-Syn peptide/protein DC sensitized vaccine approach is both effective in inducing anti-α-Syn immune responses as well as reducing some clinical manifestation of PD in an appropriate Tg model. The mechanism for the reduction in brain levels of IL-1α after α-Syn sensitized DC vaccination is unclear. However, there is evidence that IL-1 stimulates the generation of inflammation inducing Th17 cells through downregulation of anti-inflammatory regulatory T cells. (Ikeda et al., 2014) This observation underscores the importance of the balance between Th17 cells and regulatory T cells in autoimmune and inflammatory diseases. (Noack et al., 2014) Therefore, it is possible that the α-Syn sensitized DC vaccine can decrease brain IL-1 α levels through the generation and activity of regulatory T cells.

In summary, the results presented in this invention show that the α-Syn recombinant protein and peptide sensitized DC vaccine tested stimulated immune responses as well as an anti-inflammatory phenotype that protected an α-Syn expressing Tg mouse model from locomotor defects. Overall, the results presented indicate the clinical utility of this α-Syn DC sensitized cell based vaccine approach against PD.

Example 5—Study Design to Test the Efficacy of Anti-α-Syn Antibodies as Passive Immunotherapy in an AAV-α-Syn Rat PD Model Several animal models have been developed which mimic many of the clinical features of PD. As indicated, it has been demonstrated that injection of an AAV vector expressing WT α-Syn into the SN of rats resulted in a 20% loss of DA neurons 4 weeks after transduction, with a further progressive loss of the neurons up to 50-60% at 2-6 months post transduction depending on the AAV serotype and amount of vector delivered. Previous studies with the AAV9-α-synuclein used here demonstrates widespread expression of α-synuclein throughout the substantia nigra associated with 50% cell loss at 2 months post delivery (Gorbatyuk et al., 2008; Decressac et al., 2012; Pabon et al., 2012). FIG. 6 summarizes the study design of the experiments presented in the present invention including: (a) the time frame for antibody delivery, blood collections and analyses and (b) the timing of the behavioral testing (c) sequence of the peptides used to generate the α-Syn specific antisera as well as (d) the kinetics of injected antibody levels. The results shown in (d) demonstrate that antibody levels remained high for at least a month.

Figure 7:
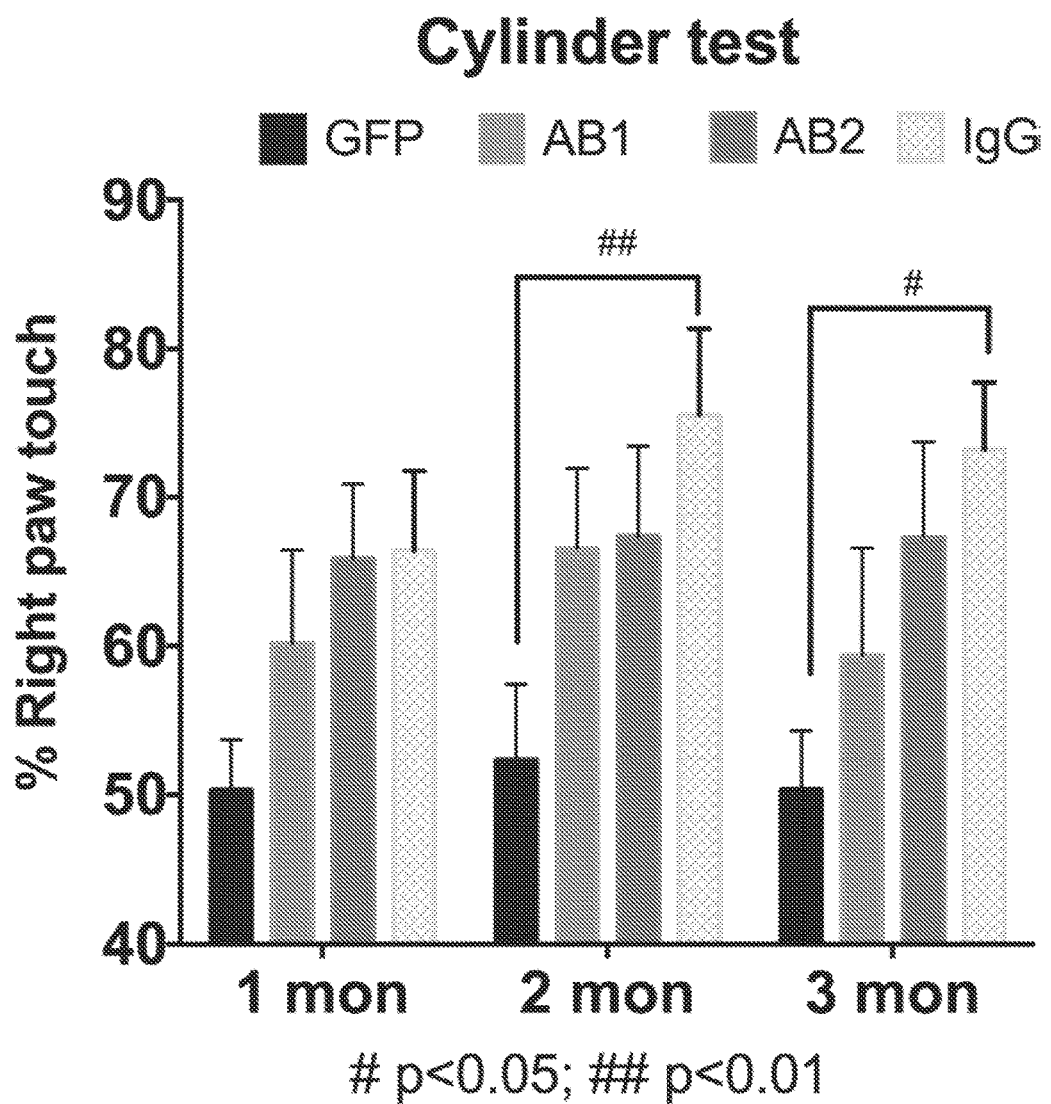
FIG. 7 shows a graph showing the effect of intraperitoneal administered anti-α-Syn antibodies on motor function. AAV-α-Syn+IgG rats demonstrated paw bias in the cylinder test when compared with AAV-GFP controls starting at two months and continued at 3 months, likely reflecting the progressive nature of this model with ongoing DA cell loss (A two-way ANOVA found a main effect of treatment, F3, 67=4.48, p=<0.001). Although AB1 or AB2 antibody treatment did not demonstrate any significant improvement in behavioral deficits compared to AAV-α-Syn+IgG treated animals, at no time was the AB1 or AB2 group significantly different from the control AAV-GFP group. Data are presented as the percent right paw preference ±SEM (n=23 AAV-GFP control and n=16 for treatment groups).

Example 6—Anti-α-Syn Antibodies Ameliorate Paw Use Bias Post AAV-α-Syn Injection The effects of anti-α-Syn antibodies on AAV-α-Syn induced motor deficits, using a cylinder paw preference test was assessed. Significant motor deficits were observed to develop over time in the IgG treated AAV-α-Syn group, compared to the control AAV9-GFP group, consistent with a progressive loss of DA neurons as we and others have observed previously (Decressac et al., 2012; Pabon et al., 2012). Paw use bias was observed in synuclein treated rats with IgG treatment beginning two months after AAV-α-Syn injection (a two-way ANOVA indicated a treatment effect of α-Syn ($F3, 67$=4.78, $p=<0.001$, Bonferonni's tests $p<0.01$). The AAV-α-Syn+IgG treated rats continued to remain different from control at both 2 and 3 months (Bonferonni's test $P<0.01$ vs GFP). (FIG. 7**, Table 1). On the other hand, the AB1 and AB2 treated groups did not demonstrate behavioral impairment that was statistically different from GFP control group during the entire study period (Bonferonni's test $P>0.05$). The performance score of AB1 treated rats was always closer to 50% than AAV-α-Syn+IgG rats but there was no statistically significant difference between the groups.

| Paw preference for all groups. | | | | |
| --- | --- | --- | --- | --- |
| | | % Right paw preference | | |
| Group name | Number of subject | 1 mon | 2 mon | 3 mon |
| AAV-GFP/PBS | 23 | 50 ± 3.9 | 52 ± 4.52 | 50 ± 3.35 |
| AAV-α-Syn + IgG | 16 | 66 ± 5.50 | 76 ± 6.00 | 73 ± 4.64 |
| AAV-α-Syn + AB1 | 16 | 60 ± 6.46 | 67 ± 5.59 | 59 ± 7.49 |
| AAV-α-Syn + AB2 | 16 | 66 ± 5.16 | 67 ± 6.28 | 67 ± 6.65 |

Example 7—Treatment with Anti-α-Syn Antibodies Reduces α-Syn Levels in the SN

Figure 8:
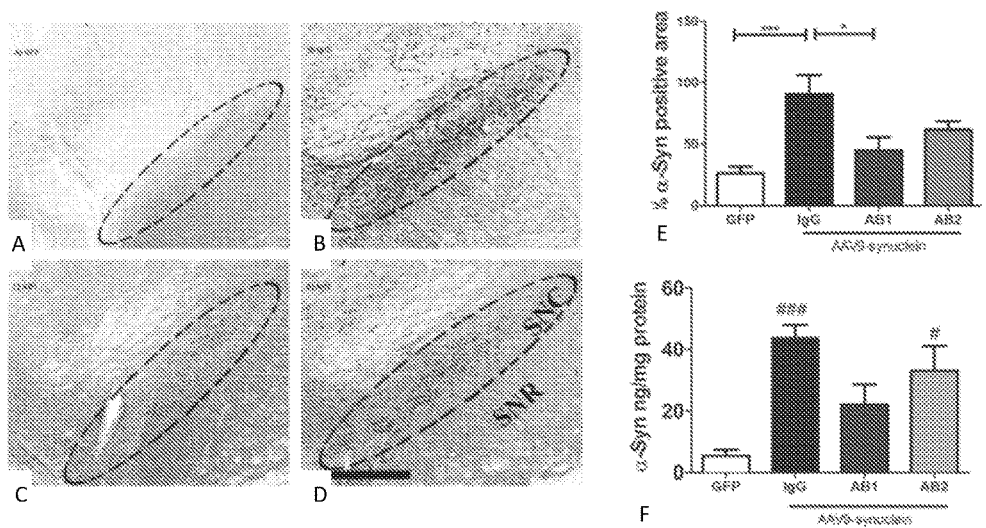
FIG. 8 shows the effect of intraperitoneal administered anti-α-Syn antibodies on AAV vector mediated α-Syn expression. Immunostaining of the substantia nigra (SN) region with an antibody against α-Syn. Administration of AAV-α-Syn into the rat SN caused significant expression of α-Syn in the SN (B) compared to the AAV-GFP control group (A). Intraperitoneal injection of anti-α-Syn antibody AB1 reduced α-Syn level in the SN (C), while injection with antibody AB2 had a reduced effect (D). Quantitative analysis of levels of α-Syn expression is presented as percent positive area (E). Data are presented as the percent positive area of anti-α-Syn staining throughout the SN (n=8 animals per group). Asterisk denotes significance (***$P<0.001$, *$P<0.05$) with comparison made to the ipsilateral AAV-GFP group by 1-way ANOVA with post-hoc Bonferroni test. ELISA analysis confirmed a significant reduction in α-Syn levels in the SN with antibody AB1 compared to IgG treatment (F). ### $P<0.001$, # $P<0.05$ vs. Control AAV-α-Syn+IgG. Data are presented as the mean concentration of α-Syn in pg/μg of protein±SEM (n=6 per group). Scale bars are 100 μm.

There was extensive expression of α-Syn in and around the AAV injection site at 3 months post AAV injection (FIG. 8B,E). Rats treated with anti-α-Syn antibodies demonstrated visibly less positive α-Syn staining in the SN than AAV-α-Syn expressing rats treated with control IgG (FIG. 8C, D). Compared to AAV-GFP, injection of AAV-α-Syn significantly increased α-Syn expression in the SN one-way ANOVA ($F (3, 27)=7.215$, $p=0.001$) (FIG. 8E). Anti-α-Syn antibody AB1 treatment significantly attenuated α-Syn accumulation compared to AAV-α-Syn+IgG (*$p<001$). ELISA based measurements using tissue homogenates from ipsilateral SN was used to further confirm the effects of the anti-α-Syn antibodies on α-Syn accumulation. Compared to AAV-α-Syn+IgG, administration of anti-α-Syn antibodies resulted in a significant reduction in α-Syn levels in the SN as analyzed by one-way ANOVA ($F (3, 21)=8.207$, $p=0.0012$) (FIG. 8F). Anti-α-Syn antibody AB1 treatment attenuated extensive α-Syn accumulation by 50% compared to AAV-α-Syn+IgG ($p<001$).

Figure 9:
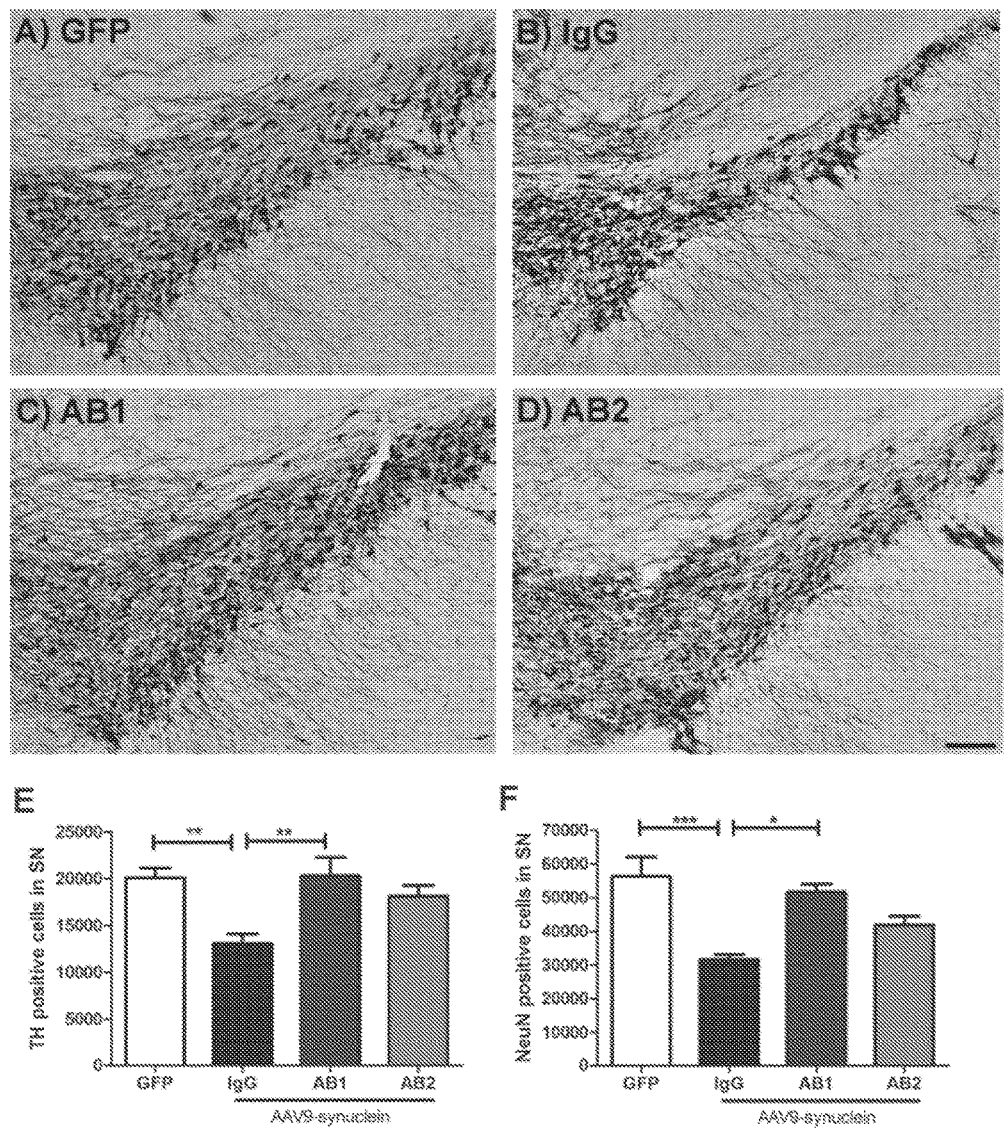
FIG. 9 shows the rescue of TH+ and NeuN+ cells in the ipsilateral SN with intraperitoneal administration of anti-α-Syn antibodies. Immunohistochemical staining of the SN region with an anti-TH antibody (A) AAV-GFP, (B) AAV-α-Syn+IgG, (C) AAV-α-Syn+AB1, (D) AAV-α-Syn+AB2. (E) Graph of unbiased stereological estimation of TH+ cells in the SN of treated animals. AB1 treated animals showed similar levels of TH+ cells compared to the GFP control and significantly higher number of TH+ cells compared to the IgG treated group. Data are shown as mean±SEM (n=13 AAV-GFP control and n=7 for treatment groups). (F) Graph of NeuN+ cells of the SN. Stereologic analysis shows a significant rescue of NeuN+ cells in SN sections with AB1 compared with IgG treated animals (n=9 AAV-GFP control and n=7 for treatment groups). *$P<0.05$, $P<0.01$, *$P<0.001$. Scale bar=100 μm.

Example 8—Anti-α-Syn Antibodies Protect Against α-Syn Induced DA Neuron and NeuN Positive Cells Loss in the SN The expression of AAV delivered α-Syn resulted in a 40% loss of TH positive cells in the SN at 3 months in the control AAV-α-Syn+IgG group (FIG. 9B,E). Unbiased stereological counting of TH positive neurons demonstrated that anti-α-Syn antibodies AB1 significantly protected neurons from AAV-α-Syn induced toxicity (one-way ANOVA ($F (3, 30)=5.8$, $p=0.002$) (FIG. 9E). These results demonstrate that the anti-α-Syn antibody AB1 was able to rescue dopaminergic neurons from death due to α-Syn mediated neurodegeneration. Since loss of TH staining can occur without the loss of neurons the number of NeuN positive cells within the SN was examined in each treatment group. Loss of NeuN positive cell counts indicates DA neuron cell death and not the down regulation of TH phenotypic changes. As expected, a significant loss of NeuN+ve neurons was observed in the SN in the AAV-α-Syn+IgG group (one-way ANOVA (one-way ANOVA ($F (3, 29)=7.92$, $p=0.002$) (FIG. 9F). As with the TH staining, the decline in the number of NeuN positive cells was not observed with AB1 treatment (FIG. 9F). As noted, with the anti-TH staining, AB2 demonstrated an intermediate rescue of NeuN positive cells compared to AB1 (treatment was not statistically different from the control group).

Example 9—Anti-α-Syn Antibodies Reduce Microglial Activation in the SN

Figure 10:
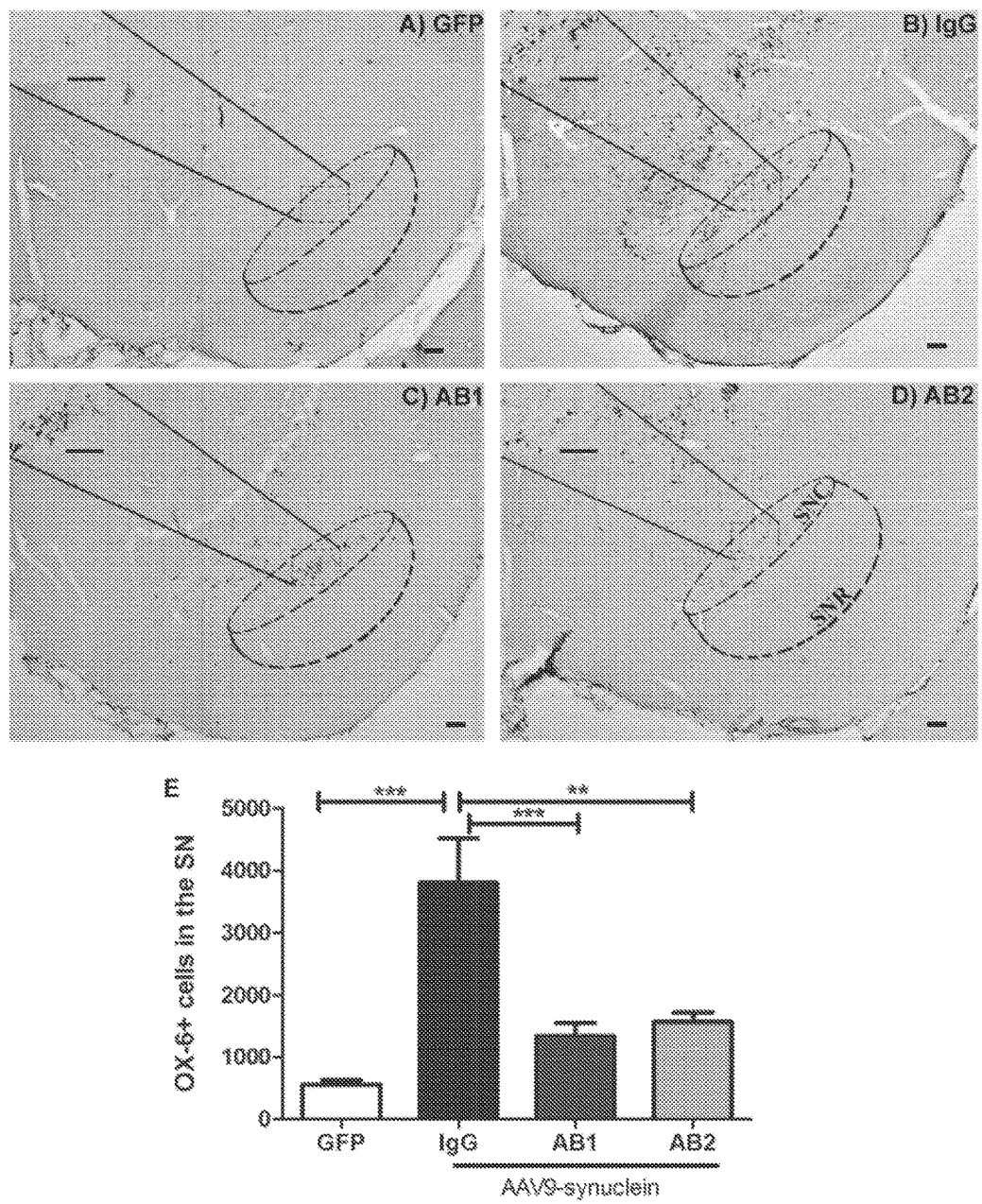
FIG. 10 shows the effect of intraperitoneal administered anti-α-Syn antibodies on the number of OX-6+ cells (MHCII). Micrographs of anti-OX6 staining for (A) AAV-GFP, (B) AAV-α-Syn+IgG, (C) AAV-α-Syn+AB1, and (D) AAV-α-Syn+AB2. Strong immunoreactivity for OX-6 is shown in the inset at high power magnification (40×). Increased OX-6 immunoreactivity was present in AAV-α-Syn+IgG treated rats compared to the other three groups. (E) Graph of unbiased stereological estimation of OX6+ cells in the SN. There is a significant decrease in the number of OX-6+ cells in groups that received anti-α-Syn antibodies (AB1, AB2) compared with the control IgG groups. Data are shown as mean±SEM. (AAV-GFP control [n=14], AAV α-Syn+IgG [n=9], AB1 [n=8], and AB2 [n=6] were analyzed) *P<0.0001P<0.001 by one-way ANOVA with post-hoc Bonferroni test. Scale bar=100 µm.

Analysis of the potential effect of α-Syn on activated microglia was made using the monoclonal antibody OX-6 which is directed against MHC II antigen, and as such can be considered to be a marker for microglial activation. Immunostaining revealed OX-6-immunopositive microglia distributed across the ipsilateral SN regions (FIG. 10). Activated microglia demonstrated the characteristic bushy morphology with increased cell body size and contracted and ramified processes. There was a significant difference between groups in the numbers of MHCII expressing cells at three months after administration of the anti-α-Syn antibodies. One-way ANOVA revealed an overall effect of anti-α-Syn antibody treatment of the SN ($F(3, 36)=16$, $p=<0.0001$). There were more activated microglia in the ipsilateral SN in all of the α-Syn treated groups; however, the numbers were lower in groups treated with the anti-α-Syn antibodies compared to AAV-α-Syn+IgG group (FIG. 10 B-E).

DISCUSSION

Advances in immunotherapy for Alzheimer's disease (AD) are now being applied to the field of Parkinson's disease (PD) research. Several years ago, the first antigen-loaded DC vaccine against AD was developed and tested in a mouse model (Cao et al., 2008). This cell-based approach to vaccination generated a long-lasting antibody response without eliciting significant inflammation. The present invention shows DCs sensitized with full length rh-α-Syn, or with peptide fragments from h-α-Syn, are effective in triggering the generation of anti-α-Syn antibodies in a Tg α-Syn mouse model of synucleinopathy.

Dendritic cell based (DC) vaccination is a cell-based therapy that elicits an immune response through the use of antigen-loaded/sensitized DCs as the vehicle for immunization. DCs have a central role in initiating primary immune responses, through the presentation of antigen to T-cells. (Banchereau and Steinman (1998); Steinman (1991)). Moreover, studies have revealed that DCs can induce proliferation of B-cells, directly stimulate production of antibodies, (Dubois et al., 1999; Dubois et al., 1997) and influence immunoglobulin class-switching.19 These findings suggest that DCs can regulate the humoral immune response. (Clark, 1997) Antigen-sensitized DCs have been evaluated as potential vaccines for cancer treatment. (Barrou et al., 2004; Cohen et al., 2005; Gajewski et al., 2001; Loveland et al., 2006; Mittendorf et al., 2006; Satthaporn et al., 2001) Other clinical trials have also been performed to evaluate their potential utility against other disorders such as infectious diseases. (Ide et al., 2006; Pellegatta et al., 2006) In fact, in animal studies, DCs sensitized with mutant Ab peptides were used to vaccinate different mouse models of AD, without eliciting a generalized inflammatory response. (Cao et al., 2008; Luo et al., 2012; Nabar et al., 2012) However, to date the only approved and licensed therapeutic vaccine using a DC based strategy is Sipuleucel-T (Provenge), used for the treatment of hormone resistant metastatic prostate carcinoma. (Wesley et al., 2012; Small et al., 2000; Sims, 2012)

Based on past work, the novel study reported here was undertaken to develop and evaluate, immunologically and therapeutically, a DC-based vaccine against human-a-Syn in a Tg mouse model of PD/synucleinopathies. An important advantage of DCs is their "self adjuvant" activity in eliciting an immune response without causing generalized inflammation which typically occurs with vaccines administered with conventional adjuvants. (Hart, 1997) Moreover, peptide-sensitized DC (PSDC) vaccines trigger longer lasting antigen-specific immune responses in comparison to traditional vaccines. (Steinman, 2001) Despite the fact that peptide-sensitized DC vaccination has many advantages, this approach has not yet been explored in a PD-related study. In the present invention, human-a-Syn (rh-a-Syn) and a-Syn peptides, containing the B cell epitopes, were used to sensitize DCs. These sensitized DCs were then used as a vaccine to evaluate immune responses in a Tg mouse model of PD that expresses a 140 amino acid full length human A53T variant a-Syn (B6; C3-Tg (Prnp-SNCA*A53T)83Vle/J), under the control of the mouse prion protein promoter. Results from this study indicate the ability of the a-Syn protein/peptide sensitized DC vaccine to elicit specific anti-a-Syn protein/peptide antibody responses. As well, these DC vaccines ameliorated the locomotor deficits which are characteristic of the a-Syn expressing Tg PD mouse model used in this investigation.

Antigenicity analysis of the peptide fragments demonstrated three major B-cell epitopes. These peptides were combined as an antigen mixture to stimulate mouse bone marrow-derived DCs with the full-length recombinant protein (rh-α-Syn) as a treatment control. The peptide fragment sensitized DCs (PSDC) elicited an earlier and more sustained antibody response than did DCs sensitized with full-length rh-α-Syn. These results indicate the peptide may pass the antigen processing procedure and can be easier seen by T cells and generate a quicker antibody response.

Epitope mapping to the anti-sera generated from the vaccinated animals verified the prediction of antigenicity. The third epitope (peptide C) appears to be the critical antigen that elicits an antibody response comparable to recombinant α-Syn. Notably, peptide C sensitized DCs resulted in the best antibody response (the highest titer against this peptide). This result highlights the importance of Peptide C and implies its importance in disease development. Peptide C may be an important target for therapy development in the future. Another explanation for this result is that antigen presentation interaction occurred when being used simultaneously, so the test to each individual peptide is necessary to identify new epitopes for vaccine development.

Rotometry testing showed that both vaccinated Tg mouse groups performed better than non-sensitized DC vaccinated Tg mice. Despite the improvement in locomotor activity in the vaccinated mice, levels of soluble brain α-Syn measured after euthanasia was not different among the groups. While it is possible that the assay fails to measure total (insoluble and soluble) α-Syn, a more likely explanation may relate to the mouse model used. The PD model heavily overexpresses α-Syn, to levels greater than those seen in physiological or pathophysiological circumstances. When used in a system that expresses normal α-Syn at pathophysiological levels, the vaccine may in fact show a reduction in total α-Syn levels. Another possibility is that the animals were not provided sufficient vaccinations, especially after 12 months of age. Herein, the last treatment was at 12 months, with euthanasia occurring at 17 months. The mouse model of synucleinopathy utilized herein does not show pathology or locomotor dysfunction until an advanced age (Fernagut and Chesselet, 2004).

A range of immunotherapies, including vaccination with Aβ peptide (Morgan et al., 2000), antigen-specific T-cells generated with Aβ (Cribbs et al., 2003), and antibodies against Aβ have all proved to be effective to some extent in Tg mouse models of AD (McLaurin, 2002). Of these approaches, vaccination still stands out as safest and least expensive. Major hurdles to vaccination are the immune tolerance associated with aging and the control of abnormal responses to vaccination. The immune system becomes impaired with aging (Weng, 2006, Shaw et al., 2010), and so active immunization requires a strong adjuvant to simulate the immune response. Unfortunately, a strong adjuvant leads to over activation of the immune system, elicitation of a massive T-cell response which in turn infiltrates the brain through a leaky blood brain barrier, culminating in an encephalitic syndrome. This scenario was observed in a subset of subjects in the AD vaccine clinical trial (Mathews and Nixon, 2003). Interestingly, a follow-up study revealed that the antibody producers attenuated progression of the disease (Mathews and Nixon, 2003).

Following the path of AD researchers, vaccines have been developed and tested in animal models of PD (Hirsch et al., 1985, Masliah et al., 2005, Mougenot et al., 2010). The traditional approach to vaccination against PD remains in the same limbo as AD vaccines because of safety concerns. Instead of preventive vaccinations, therapeutic vaccination may be more reliable in terms of safety and efficiency. Dendritic vaccines might offer the best approach for the neurodegenerative diseases of AD and PD. Dendritic cell vaccines have been widely studied and are currently being applied for treatment of cancers. Significant advantages of dendritic cell vaccines include: a) their ability to serve as self-adjuvants with no additional stimulation of the immune system required; b) the antigen processing occurs ex vivo in cell culture and hence there is no direct antigen-induced inflammation in the host; c) dendritic cells are collected from patient's own blood and hence there is no potential for tissue rejection. Moreover, previous data show that DC vaccines skew the immune response towards a Th2 anti-inflammatory response as opposed to a Th1 inflammatory response (Luo et al., 2012, Nabar et al., 2012).

The present invention identifies the most effective peptide fragments of α-Syn with which to vaccinate to successfully produce anti α-Syn antibodies in the context of a DC vaccine. In addition, the present invention shows an absence of generalized inflammation indicated by no significant changes in a panel of plasma pro-inflammatory cytokines, an indication of its safety and possible immune modulating effects compared to standard adjuvant-based vaccinations. Since antigen sensitized DCs as vaccine can target the pathological protein and modulate the immune system, the peptide DC vaccine is a possible treatment for PD.

In order to identify a novel epitope to use for vaccine development, we generated several antibodies to major α-Syn epitopes and evaluated targeted passive immunotherapy. Of particular interest were antibodies which were directed against regions not previously tested in an animal model of PD pathology. These were designated AB1 (against N-terminal) and AB2 (against the mid region of α-Syn). An established PD model of AAV mediated over expression of human α-Syn was examined within the rat SN. This model, importantly, induces a progressive PD-like pathology (Gorbatyuk et al., 2008; Decressac et al., 2012; Pabon et al., 2012). In the control experiment (AAV-α-Syn+non-immune IgG administration), a 40% reduction in TH+ cells in the SN was observed, which is consistent with previous reports of this model (Gorbatyuk et al., 2008; Decressac et al., 2012; Pabon et al., 2012) In the experimental groups novel polyclonal antibodies generated against two identified putative B cell epitopes within the N-terminal and central regions of human α-Syn were administered to the α-Syn expressing rats. It was observed that the AB1 anti-α-Syn antibodies could prevent α-Syn induced DA cell loss and improve behavioral outcomes, whereas AB2 was less effective. Rats expressing α-Syn without any anti-α-Syn AB treatment demonstrate significant paw use bias using a cylinder test starting at two months when compared to animals expressing AAV-GFP (controls). Rats expressing α-Syn and treated with the anti-α-Syn AB1 or AB2 antibody showed a trend towards amelioration of this behavioral deficit as they were not significantly different from the control AAV-GFP treatment group at any time point. Taken together, this would suggest that AB1 may be a better target region (N-terminus) as this antibody seems to alter the progression of the overall deficit more effectively than AB2 (central domain).

More importantly, we observed a significant rescue of α-Syn mediated TH+ and NeuN+ neuron loss in the SN after treatment with the AB1 antibody. The AB1 treatment was identical to the GFP control group and statistically different from the IgG treated group. Treatment with the AB2 antibody trended toward an amelioration of neuron loss but was not statistically significant from either the untreated or GFP expressing control groups, again suggesting that the AB1 epitope might be a better target for development of immunotherapies than the AB2 epitope. The intermediate rescue of neuron loss in the AB2 treated animals would suggest that this antibody is less efficacious.

Microglial activation is well established in many neurological diseases including PD. We examined the level of microglial activation with the MHCII marker, OX-6. We observed a significant increase in OX-6 staining in our α-Syn over expressing model (FIG. 10) (Pabon et al., 2012). More interestingly, we observed a reduction in the number of activated microglia in α-Syn expressing rats treated with either the AB1 or AB2 antibodies. This reduction is likely due to the decrease in toxic α-Syn species present in the brain and thus the reduction in neuron cell death due to α-Syn.

Recently therapeutic efficacy with three different anti-α-Syn antibodies, directed against the C-terminal region of α-Syn, has been reported (Ghochikyan et al., 2014). These investigators determined that antibodies induced by the peptide α-Syn126-140 immunoprecipitated higher levels of α-Syn from brain extracts than the other two antibodies tested. In contrast to the Ghochikyan et al. study we, as indicated, generated antibodies directed against the N-terminal and central regions of human α-Syn. It has been well documented that the N-terminal amino acids are essential for formation of amphipathic alpha-helix responsible for α-Syn membrane recognition (Bartels et al., 2010). Deletion of N-terminal amino acids have shown not only decreases in the helix propensity of α-Syn but also reductions in the toxicity of α-Syn protein in yeast (Vamvaca et al., 2009). This implies that the N-terminal amino acids may initiate the folding of the entire α-Syn protein and promote formation of toxic α-Syn protein. As indicated above, both of the anti-α-Syn antibodies generated by the present invention reduced the α-Syn level within the brain. However, the N-terminal targeted AB1 antibody proved more efficacious than the central domain epitope (AB2). Others have demonstrated that an antibody against N-terminus amino acids 1-5 of α-Syn has the ability to reduce pathology in α-Syn mouse model (Tran et al., 2014). This epitope is distinct from the region studied in the present invention. Thus, targeting the N-terminal region of α-Syn protein might represent a useful immunotherapeutic approach to treat PD as well as other α-synucleinopathies.

There are several potential mechanisms for antibody mediated clearance of α-Syn. Firstly, the peripheral sink hypothesis proposes a shift of the α-Syn equilibrium from the central nervous system to the peripheral blood. This is based on the now well established observation that there is a dysfunctional blood brain barrier (BBB) in PD patients (Kortekaas et al., 2005). In this model abnormal α-Syn protein is envisioned to enter into the peripheral circulation through a "leaky" BBB with subsequent activation through antigen-presenting cells resulting in the induction of adaptive immune responses. Thus, these antibodies may exert their effect in the brain by reducing the levels of α-Syn load in the periphery which, in turn, reduces the accumulation of α-Syn in the brain (Zhang et al., 2011). Second, an alternative mechanism for clearance of α-Syn by anti-α-Syn antibodies may involve the formation of extracellular immune complexes with secreted α-Syn leading to microglial activation. It has been determined that the MHCII protein is critical for α-syn induced microglial activation, IgG deposition, and CD4 T cell proliferative responses (Harms et al., 2013). In fact, it has been demonstrated that that MHCII knockout mice are protected from α-Syn induced dopaminergic neurodegeneration (Harms et al., 2013). Eun-Jin Bae and colleagues recently employed a passive immunotherapy approach to test the efficacy of anti-α-Syn antibodies in the clearance of extracellular α-Syn aggregates in microglial cells (Bae et al., 2012). These authors demonstrated that these anti-α-Syn antibodies block cell to cell transfer of extracellular α-Syn by promoting α-Syn acquisition into microglia, which were then delivered to the lysosome for destruction. Targeting extracellular α-Syn may reduce the likelihood of adverse functions of proteins inside the neuronal cytoplasm and would be a unique approach for treating the consequences of abnormal α-Syn deposition. But, microglial activation and functional shifting are questions that remain to be resolved. Guo and Lee have reported that α-Syn possesses cell-to-cell transmission ability. They hypothesize that functional antibodies may reduce pathology, at least in part, by inhibiting this cell transmission process (Tran et al., 2014; Guo et al., 2014). We have also demonstrated that the function of microglia is restored after antibody treatment, potentially allowing microglia to more effectively digest α-Syn to prevent disease progression.

Vaccine and immunotherapy strategies have been determined to be effective in animal models of neurodegenerative diseases such as PD and AD, but have failed in clinical trials targeting specifically Aβ in AD, due to both safety and efficacy concerns (Valera et al., 2013; Lemere, 2013). Although not completely without drawbacks the passive immunotherapy may have several advantages. Firstly, the dose can be controlled by monitoring blood antibody levels with subsequent cessation of treatment if there are any adverse reactions. Secondly, a cocktail of different epitope specific antibodies may offer a more effective therapy. Despite these advantages, certain issues need to be overcome in order to assess their long-term clinical safety and efficacy. To ensure adequate amounts of efficacious antibodies in the brain, these antibodies need to cross the blood brain barrier easily (Yu et al., 2013). A second major hurdle would be that repeated injection of antibodies over time may lead to the formation of antibodies against the previously administered antibody which could potentially neutralize their potentially beneficial effects and/or lead to serious side effects (Liu et al., 2014). Assessment of the risks associated with the use of these polyclonal antibodies need to be evaluated, and necessary steps taken to identify and minimize potential adverse effects. One potential method for reducing adverse effects would be the use of humanized antigen specific monoclonal antibodies for use as therapeutic agents. In order to obtain an optimal therapeutic effect, these antibodies may require administration prophylactically at earlier onset of PD pathological changes.

The passive immunotherapy approach has been an attractive potential strategy for the treatment of PD. The present invention indicates that passive immunotherapy targeting α-Syn is a therapeutic approach for slowing the progression of symptoms of PD. Further, the present invention shows that targeting of the N-terminal domain is a more effective treatment than targeting the central domain of α-Syn. This may be because the N-terminal domain is more structured and therefore offers a better therapeutic target than other regions of the α-Syn protein.

It is to be appreciated that the foregoing Detailed Description section, and not the Abstract section, is intended to be used to interpret the claims. The Abstract section may set forth one or more, but not all, exemplary embodiments of the present invention as contemplated by the inventor(s), and thus, is not intended to limit the present invention and the appended claims in any way.

The foregoing description of the specific embodiments should fully reveal the general nature of the invention so that others can, by applying knowledge within the skill of the art, readily modify and/or adapt for various applications such specific embodiments, without undue experimentation, without departing from the general concept of the present invention. Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents. Moreover, the breadth and scope of the present invention should not be limited by any of the above-described exemplary embodiments, but should similarly be defined only in accordance with the following claims and their equivalents. Without further elaboration, it is believed that one skilled in the art can, using the preceding description, utilize the present invention to its fullest extent.

REFERENCES

Damier P, Hirsch E C, Agid Y, Graybiel A M. The substantia nigra of the human brain. II. Patterns of loss of dopamine-containing neurons in Parkinson disease. Brain 1999; 122 (Pt 8):1437-48; PMID:10430830

Bernheimer H, Birkmayer W, Hornykiewicz O, Jellinger K, Seitelberger F. Brain dopamine and the syndromes of Parkinson and Huntington. Clinical, morphological and neurochemical correlations. J Neurol Sci 1973; 20:415-55; PMID:4272516

Spillantini M G, Crowther R A, Jakes R, Hasegawa M, Goedert M. α-Synuclein in filamentous inclusions of Lewy bodies from Parkinson disease and dementia with lewy bodies. Proc Natl Acad Sci USA 1998; 95:6469-73; PMID:9600990

Braak H, Del Tredici K, Bratzke H, Hamm-Clement J, Sandmann-Keil D, Rub U. Staging of the intracerebral inclusion body pathology associated with idiopathic Parkinson disease (preclinical and clinical stages). J Neurol 2002; 249 Suppl 3):III/1-5; PMID:11954855

Brochard V, Combadiere B, Prigent A, Laouar Y, Perrin A, Beray-Berthat V, Bonduelle O, Alvarez-Fischer D, Callebert J, Launay J M, et al. Infiltration of CD4C lymphocytes into the brain contributes to neurodegeneration in a mouse model of Parkinson disease. J Clin Invest 2009; 119:182-92; PMID:19104149

Berardelli A, Rothwell J C, Thompson P D, Hallett M. Pathophysiology of bradykinesia in Parkinson disease. Brain 2001; 124:2131-46; PMID:11673316

Tran H T, Chung C H, Iba M, Zhang B, Trojanowski J Q, Luk K C, Lee V M. Alpha-synuclein immunotherapy blocks uptake and templated propagation of misfolded α-synuclein and neurodegeneration. Cell Rep 2014; 7:2054-65; PMID:24931606;

Masliah E, Rockenstein E, Mante M, Crews L, Spencer B, Adame A, Patrick C, Trejo M, Ubhi K, Rohn T T, et al. Passive immunization reduces behavioral and neuropathological deficits in an α-synuclein transgenic model of Lewy body disease. PloS One 2011; 6: e19338; PMID: 21559417;

Games D, Valera E, Spencer B, Rockenstein E, Mante M, Adame A, Patrick C, Ubhi K, Nuber S, Sacayon P, et al. Reducing C-terminal-truncated α-synuclein by immunotherapy attenuates neurodegeneration and propagation in Parkinson disease-like models. J Neurosci 2014; 34:9441-54; PMID:25009275

Schneeberger A, Mandler M, Mattner F, Schmidt W. Vaccination for Parkinson disease. Parkinsonism Relat Disord 2012; 18 Suppl 1:S11-3; PMID:22166404

Sanchez-Guajardo V, Annibali A, Jensen P H, Romero-Ramos M. α-Synuclein vaccination prevents the accumulation of parkinson disease-like pathologic inclusions in striatum in association with regulatory T cell recruitment in a rat model. J Neuropathol Exp Neurol 2013; 72:624-45; PMID:23771222

Mougenot A L, Betemps D, Hogeveen K N, Kovacs G G, Chouaf-Lakhdar L, Milhavet O, Lehmann S, Legastelois S, Pin J J, Baron T G. Production of a monoclonal antibody, against human a-synuclein, in a subpopulation of C57BL/6J mice, presenting a deletion of the α-synuclein locus. J Neurosci Methods 2010; 192:268-76; PMID:20709102

Masliah E, Rockenstein E, Adame A, Alford M, Crews L, Hashimoto M, Seubert P, Lee M, Goldstein J, Chilcote T, et al. Effects of α-synuclein immunization in a mouse model of Parkinson disease. Neuron 2005; 46:857-68; PMID:15953415

Hirsch E, Ruberg M, Dardenne M, Portier M M, Javoy-Agid F, Bach J F, Agid Y. Monoclonal antibodies raised against Lewy bodies in brains from subjects with Parkinson disease. Brain Res 1985; 345:374-8; PMID:2994847

Banchereau J, Steinman R M. Dendritic cells and the control of immunity. Nature 1998; 392:245-52; PMID:9521319

Steinman R M. The dendritic cell system and its role in immunogenicity. Annual Rev Immunol 1991; 9:271-96; PMID:1910679

Dubois B, Bridon J M, Fayette J, Barthelemy C, Banchereau J, Caux C, Briere F. Dendritic cells directly modulate B cell growth and differentiation. J Leukoc Biol 1999; 66:224-30; PMID: 10449158

Dubois B, Vanbervliet B, Fayette J, Massacrier C, Van Kooten C, Briere F, Banchereau J, Caux C. Dendritic cells enhance growth and differentiation of CD40-activated B lymphocytes. J Exp Med 1997; 185:941-51; PMID: 9120400

Fayette J, Dubois B, Vandenabeele S, Bridon J M, Vanbervliet B, Durand I, Banchereau J, Caux C, Briere F. Human dendritic cells skew isotype switching of CD40-activated naive B cells towards IgA1 and IgA2. J Exp Med 1997; 185:1909-18; PMID: 9166420

Clark E A. Regulation of B lymphocytes by dendritic cells. J Exp Med 1997; 185:801-3; PMID:9120385

Barrou B, Benoit G, Ouldkaci M, Cussenot O, Salcedo M, Agrawal S, Massicard S, Bercovici N, Ericson M L, Thiounn N. Vaccination of prostatectomized prostate cancer patients in biochemical relapse, with autologous dendritic cells pulsed with recombinant human PSA. Cancer Immunol Immunother 2004; 53:453-60; PMID:14760510

Cohen S, Haimovich J, Hollander N. B-cell lymphoma and myeloma protection induced by idiotype vaccination with dendritic cells is mediated entirely by T cells in mice. J Immunother 2005; 28:461-6; PMID:16113602

Gajewski T F, Fallarino F, Ashikari A, Sherman M. Immunization of HLA-A2C melanoma patients with MAGE-3 or MelanA peptide-pulsed autologous peripheral blood mononuclear cells plus recombinant human interleukin 12. Clin Cancer Res 2001; 7:895s-901s; PMID:11300489

Loveland B E, Zhao A, White S, Gan H, Hamilton K, Xing P X, Pietersz G A, Apostolopoulos V, Vaughan H, Karanikas V, et al. Mannan-MUC1-pulsed dendritic cell immunotherapy: a phase I trial in patients with adenocarcinoma. Clin Cancer Res 2006; 12:869-77; PMID: 16467101

Mittendorf E A, Storrer C E, Foley R J, Harris K, Jama Y, Shriver C D, Ponniah S, Peoples G E. Evaluation of the HER2/neu-derived peptide GP2 for use in a peptide-based breast cancer vaccine trial. Cancer 2006; 106:2309-17; PMID:16596621

Satthaporn S, Eremin O. Dendritic cells (II): Role and therapeutic implications in cancer. J R Coll Surg Edinb 2001; 46:159-67; PMID:11478013

Ide F, Nakamura T, Tomizawa M, Kawana-Tachikawa A, Odawara I, Hosoya N, Iwamoto A. Peptide-loaded dendritic-cell vaccination followed by treatment interruption for chronic HIV-1 infection: a phase 1 trial. J Med Viroi 2006; 78:711-8; PMID:16628588

Pellegatta S, Poliani P L, Corno D, Grisoli M, Cusimano M, Ubiali F, Baggi F, Bruzzone M G, Finocchiaro G. Dendritic cells pulsed with glioma lysates induce immunity against syngeneic intracranial gliomas and increase survival of tumor-bearing mice. Neurol Res 2006; 28:527-31; PMID:16808884

Cao C, Lin X, Zhang C, Wahi M M, Wefes I, Arendash G, Potter H. Mutant amyloid-b-sensitized dendritic cells as Alzheimer disease vaccine. J Neuroimmunol 2008; 200: 1-10; PMID:18649951

Luo Z, Li J, Nabar N R, Lin X, Bai G, Cai J, Zhou S F, Cao C, Wang J. Efficacy of a therapeutic vaccine using mutated b-amyloid sensitized dendritic. J Neuroimmune Pharmacol 2012; 7:640-55; PMID:22684353

Nabar N R, Yuan F, Lin X, Wang L, Bai G, Mayl J, Li Y, Zhou S F, Wang J, Cai J, et al. Cell therapy: a safe and efficacious therapeutic treatment for Alzheimer disease in APPCPS1 mice. PloS One 2012; 7:e49468; PMID: 23226497

Wesley J D, Whitmore J, Trager J, Sheikh N. An overview of sipuleucel-T: autologous cellular immunotherapy for prostate cancer. Hum Vaccin Immunother 2012; 8:520-7; PMID:22370520

Small E J, Fratesi P, Reese D M, Strang G, Laus R, Peshwa M V, Valone F H. Immunotherapy of hormonerefractory prostate cancer with antigen-loaded dendritic cells. J Clin Oncol 2000; 18:3894-903; PMID:11099318

Sims R B. Development of sipuleucel-T: autologous cellular immunotherapy for the treatment of metastatic castrate resistant prostate cancer. Vaccine 2012; 30:4394-7; PMID:22122856

Hart D N. Dendritic cells: unique leukocyte populations which control the primary immune response. Blood 1997; 90:3245-87; PMID:9345009

Steinman R M. Dendritic cells and the control of immunity: enhancing the efficiency of antigen presentation. Mt Sinai J Med 2001; 68:160-6; PMID:11373688

Shaftel S S, Griffin W S, O'Banion M K. The role of interleukin-1 in neuroinflammation and Alzheimer disease: an evolving perspective. J Neuroinflammation 2008; 5:7; PMID:18302763

Hirsch E C, Hunot S. Neuroinflammation in Parkinson disease: a target for neuroprotection? Lancet Neurol 2009; 8:382-97; PMID:19296921

Basu A, Krady J K, Levison S W. Interleukin-1: a master regulator of neuroinflammation. J Neurosci Res 2004; 78:151-6; PMID:15378607

Fernagut P-O, Chesselet M-F. Alpha-synuclein and transgenic mouse models. Neurobiol Dis 2004; 17:123-30; PMID:15474350

Morgan D, Diamond D M, Gottschall P E, Ugen K E, Dickey C, Hardy J, Duff K, Jantzen P, DiCarlo G, Wilcock D, et al. A[b] peptide vaccination prevents memory loss in an animal model of Alzheimer disease. Nature, 2000; 408:982-5; PMID:11140686

McLaurin J, Cecal R, Kierstead M E, Tian X, Phinney A L, Manea M, French J E, Lambermon M H, Darabie A A, Brown M E; et al. Therapeutically effective antibodies against amyloid-[b] peptide target amyloid-[b] residues 4-10 and inhibit cytotoxicity and fibrillogenesis. Nat Med 2002; 8:1263-9.

Vasilevko V, Head E. Immunotherapy in a natural model of Abeta pathogenesis: the aging beagle. CNS Neurol Disord Drug Targets 2009; 8:98-113; PMID:19355931

Cicin-Sain L, Smyk-Pearson S, Currier N, Byrd L, Koudelka C, Robinson T, Swarbrick G, Tackitt S, Legasse A, Fischer M, et al. Loss of naive T cells and repertoire constriction predict poor response to vaccination in old primates. J Immunol 2010; 184:6739-45

Sela M, Arnon R, Schechter B. Therapeutic vaccines: realities of today and hopes for the future. Drug Discov Today 2002; 7:664-73; PMID:12110243

Masliah E, Rockenstein E, Adame A, Alford M, Crews L, Hashimoto M, Seubert P, Lee M, Goldstein J, Chilcote T, et al. Effects of a-synuclein immunization in a mouse model of Parkinson disease. Neuron 2005; 46:857-68; PMID:15953415

Bachy V, Ballerini C. Gourdain P, Prignon A, Iken S, Antoine N, Rosset M, Carnaud C. Mouse vaccination with dendritic cells loaded with prion protein peptides overcomes tolerance and delays scrapie. J Gen Virol 2010; 91:809-20; PMID:19864503

Okano F, Merad M, Furumoto K, Engleman E G. In vivo manipulation of dendritic cells overcomes tolerance to unmodified tumor-associated self antigens and induces potent antitumor immunity. J Immunol 2005; 174:2645-52

Farag M M, Tedjokusumo R, Flechtenmacher C, Asen T, Stremmel W, Muller M, Protzer Weigand K. Immune tolerance against HBV can be overcome in HBV transgenic mice by immunization with dendritic cells pulsed by HBVsvp. Vaccine 2012; 30:6034-9; PMID:22867720

Morgan D, Diamond D M, Gottschall P E, Ugen K E, Dickey C, Hardy J, Duff K, Jantzen P, DiCarlo G, Wilcock D, et al. A b peptide vaccination prevents memory loss in an animal model of Alzheimer disease. Nature 2000; 408:982-5; PMID:11140686

Yu J S, Liu G, Ying H, Yong W H, Black K L, Wheeler C J. Vaccination with tumor lysate-pulsed dendritic cells elicits antigen-specific, cytotoxic T-cells in patients with malignant glioma. Cancer Res 2004; 64:4973-9; PMID:15256471

Nair S K, Heiser A, Boczkowski D, Majumdar A, Naoe M, Lebkowski J S, Vieweg J, Gilboa E. Induction of cytotoxic T cell responses and tumor immunity against unrelated tumors using telomerase reverse transcriptase RNA transfected dendritic cells. Nat Med 2000; 6:1011-7; PMID:10973321

Gruber A, Chalmers A S, Rasmussen R A, Ong H, Popov S, Andersen J, Hu S L, Ruprecht R M. Dendritic cell-based vaccine strategy against human immunodeficiency virus clade C: skewing the immune response toward a helper T cell type 2 profile. Viral Immunol 2007; 20:160-9; PMID: 17425430

Boscardin S B, Hafalla J C, Masilamani R F, Kamphorst A O, Zebroski H A, Rai U, Morrot A, Zavala F, Steinman R M, Nussenzweig R S, et al. Antigen targeting to dendritic cells elicits long-lived T cell help for antibody responses. J Exp Med 2006; 203:599-606; PMID:16505139

Nabar N R, Yuan F, Lin X, Wang L, Bai G, Mayl J, Li Y, Zhou S F, Wang J, Cai J, et al. Cell therapy: a safe and efficacious therapeutic treatment for Alzheimer disease in APPCPS1 mice. PLoS One, 2012; 7:e49468

Luo Z, Li J, Nabar N R, Lin X, Bai G, Cai J, Zhou S F, Cao C, Wang J. Efficacy of a therapeutic vaccine using mutated b-amyloid sensitized dendritic cells in Alzheimer mice. J Neuroimmune Pharmacol 2012; 7:640-55; PMID: 22684353

Ikeda S, Saijo S, Murayama M A, Shimizu K, Akitsu A, Iwakura Y. Excess IL-1 signaling enhances the development of Th17 cells by downregulating TGF-b-induced Foxp3 expression. J Immunol 2014; 192:1449-58

Noack M, Miossec P. Th17 and regulatory T cell balance in autoimmune and inflammatory diseases. Autoimmun Rev 2014; 13:668-77; PMID:24418308

Giasson B I, Duda J E, Quinn S M, Zhang B, Trojanowski J Q, Lee V M. Neuronal a-synucleinopathy with severe movement disorder in mice expressing A53T human a-synuclein. Neuron 2002; 34:521-33; PMID:12062037

Cao C, Lin X, Zhang C, Wahi M, Wefes I, Arendash G, Potter H. Mutant amyloid-b-sensitized dendritic cells as Alzheimer disease vaccine. J Neuroimmunol 2008; 200: 1-10; PMID:18649951

Rozas G, Guerra M J, Labandeira-Garcia J L. An automated rotarod method for quantitative drug-free evaluation of overall motor deficits in rat models of parkinsonism. Brain Res Brain Res Protoc 1997; 2:75-84; PMID: 9438075

Meredith G E, Kang U J. Behavioral models of Parkinson disease in rodents: a new look at an old problem. Mov Disord 2006; 21:1595-606; PMID:16830310

Cao C, Lin X, Wahi M M, Jackson E A, Potter H, Jr. Successful adjuvant-free vaccination of BALB/c mice with mutated amyloid b peptides. BMC Neurosci. England, 2008; 9:25

All publications and patent documents cited in this application are incorporated by reference in pertinent part for all purposes to the same extent as if each individual publication or patent document were so individually denoted and to the extent that their teachings are not inconsistent with explicit teachings herein. By citation of various references in this document, Applicants do not admit any particular reference is "prior art" to their invention.

We claim:

1. A method of treating symptoms of Parkinson's Disease in a subject, comprising
   sensitizing a dendritic cell to at least one peptide fragment of an α-synuclein protein, which peptide fragment is selected from the amino acid sequences of SEQ ID NO:1, SEQ ID NO:2, SEQ ID NO:3, and any combination thereof; and
   administering to the subject the sensitized dendritic cell.

2. The method of claim 1, wherein the at least one peptide fragment of the α-synuclein protein is the amino acid sequence of SEQ ID NO:1.

3. The method of claim 1, wherein the at least one peptide fragment of the α-synuclein protein is the amino acid sequence of SEQ ID NO:2.

4. The method of claim 1, wherein the at least one peptide fragment of the α-synuclein protein is the amino acid sequence of SEQ ID NO:3.

5. The method of claim 1, wherein the dendritic cell is autologous.

6. The method of claim 5, wherein the dendritic cell is obtained from the subject by leukapheresis.

7. The method of claim 1, wherein the subject is a human.

8. A method of inhibiting α-synuclein mediated neurodegeneration in a subject, comprising
   sensitizing a dendritic cell to at least one peptide fragment of an α-synuclein protein, which peptide fragment is selected from the amino acid sequences of SEQ ID NO:1, SEQ ID NO:2, SEQ ID NO:3, and any combination thereof; and
   administering to the subject the sensitized dendritic cell, whereby cell death of dopaminergic neurons is inhibited.

9. The method of claim 8, wherein the neurodegeneration is induced by Parkinson's Disease.

10. The method of claim 8, wherein the at least one peptide fragment of the α-synuclein protein is the amino acid sequence of SEQ ID NO:1.

11. The method of claim 8, wherein the at least one peptide fragment of the α-synuclein protein is the amino acid sequence of SEQ ID NO:2.

12. The method of claim 8, wherein the at least one peptide fragment of the α-synuclein protein is the amino acid sequence of SEQ ID NO:3.

13. The method of claim 8, wherein the dendritic cell is autologous.

14. The method of claim 13, wherein the dendritic cell is obtained from the subject by leukapheresis.

15. The method of claim 8, wherein the subject is a human.

* * * * *

UNITED STATES PATENT AND TRADEMARK OFFICE
CERTIFICATE OF CORRECTION

PATENT NO. : 10,155,030 B2
APPLICATION NO. : 15/313810
DATED : December 18, 2018
INVENTOR(S) : Chuanhai Cao and Xiaoyang Lin It is certified that error appears in the above-identified patent and that said Letters Patent is hereby corrected as shown below:

In the Specification

Column 11,
Lines 8-9, "human subject. In another aspect," should read --human subject.
                                                                                  In another aspect,--.

Column 14,
Line 65, "Brian" should read --Brain--.

Column 18,
Line 16, "a- Syn peptide/a-Syn" should read --α-Syn peptide/ α-Syn--.
Line 24, "a- Syn mice" should read --α-Syn mice--.
Lines 25-26, "against rh-a-Syn" should read --against rh-α-Syn--.

Column 19,
Line 1, "lateney" should read --latency--.
Lines 1-2, "Tg-rh-a-Syn vaccinated mice" should read --Tg-rh-α-Syn vaccinated mice--.
Line 6, "of the a-Syn expressing Tg mice" should read --of the α-Syn expressing Tg mice--.
Line 46, "vaccinated αSyn" should read --vaccinated α-Syn--.
Line 50, "control, Tg rh-αSyn DC" should read --control, Tg-rh-α-Syn DC--.
Lines 52-53, "brains of Tg rh-αSyn DC" should read --brains of Tg-rh-α-Syn DC--.
Line 56, "αSyn peptides or full-length αSyn" should read --α-Syn peptides or full-length α-Syn--.

Column 21,
Line 43, "trial, an immune based strategies" should read --trial, immune based strategies--.

Column 25,
Line 37, "human-a-Syn" should read --human-α-Syn--.
Lines 48-49, "human-a-Syn (rh-a-Syn) and a-Syn peptides," should read --human-α-Syn (rh-α-Syn) and α-Syn peptides,--.

Signed and Sealed this
Thirtieth Day of July, 2019

Andrei Iancu
*Director of the United States Patent and Trademark Office*

CERTIFICATE OF CORRECTION (continued)
U.S. Pat. No. 10,155,030 B2

Line 53, "variant a-Syn" should read --variant α-Syn--.
Lines 55-56, "of the a-Syn protein/peptide" should read --of the α-Syn protein/peptide--.
Lines 56-57, "anti-a-Syn protein/peptide" should read --anti-α-Syn protein/peptide--.
Line 59, "of the a-Syn expressing" should read --of the α-Syn expressing--.

Column 27,
Line 38, "2012) In" should read --2012). In--.

Column 28,
Line 47, "model abnormal" should read --model, abnormal--.
Line 59, "for α-syn induced" should read --for α-Syn induced--.